(12) United States Patent
Shiono

(10) Patent No.: US 7,780,702 B2
(45) Date of Patent: Aug. 24, 2010

(54) SUTURE TOOL

(75) Inventor: Junji Shiono, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 423 days.

(21) Appl. No.: 11/711,265

(22) Filed: Feb. 27, 2007

(65) Prior Publication Data

US 2008/0208218 A1    Aug. 28, 2008

(51) Int. Cl.
    *A61B 17/04*      (2006.01)
    *A61B 17/08*      (2006.01)
    *A61B 17/10*      (2006.01)

(52) U.S. Cl. ........................... 606/232; 606/151

(58) Field of Classification Search .............. 606/232, 606/148, 151, 142, 157, 158, 120, 143, 139; 623/23.72; 24/115 R, 130, 132 R, 132 AA, 24/132 WL, 115 A, 115 G, 16 R; 132/278, 132/263

See application file for complete search history.

(56) References Cited

U.S. PATENT DOCUMENTS

| | | | | |
|---|---|---|---|---|
| 2,583,530 A | * | 1/1952 | Hasselbohm | 439/395 |
| 3,673,640 A | * | 7/1972 | Brown | 24/30.5 R |
| 4,217,902 A | * | 8/1980 | March | 606/221 |
| 5,779,720 A | * | 7/1998 | Walder-Utz et al. | 606/151 |
| 6,099,553 A | * | 8/2000 | Hart et al. | 606/232 |
| 6,165,204 A | | 12/2000 | Levinson et al. | |
| 6,648,903 B1 | * | 11/2003 | Pierson, III | 606/232 |
| 2004/0236372 A1 | * | 11/2004 | Anspach et al. | 606/232 |
| 2004/0249392 A1 | * | 12/2004 | Mikkaichi et al. | 606/142 |
| 2007/0073320 A1 | | 3/2007 | Mikkaichi et al. | |
| 2007/0118163 A1 | * | 5/2007 | Boudreaux et al. | 606/157 |
| 2007/0276437 A1 | * | 11/2007 | Call et al. | 606/232 |

FOREIGN PATENT DOCUMENTS

| | | | |
|---|---|---|---|
| EP | 1484023 | * | 8/2004 |
| EP | 1 484 023 A1 | | 12/2004 |
| GB | 2 112 648 A | | 7/1983 |
| GB | 2112648 | * | 7/1983 |
| JP | 2004-358046 | | 12/2004 |
| WO | WO 99/59476 | * | 11/1999 |
| WO | WO 2007/005394 A1 | | 1/2007 |

\* cited by examiner

*Primary Examiner*—Julian W Woo
*Assistant Examiner*—Christopher L Templeton
(74) *Attorney, Agent, or Firm*—Scully, Scott, Murphy & Presser, P.C.

(57) ABSTRACT

A suture tool is provided in which the fixing member includes: a base portion which has a thin and longitudinal plate shape and which has a through-hole through which the suture thread passes; and a pair of bent pieces of which ends are opposed to each other by bending both ends of the base portion toward the center thereof. Thick plate portions which are thick in an insertion direction of the suture thread and which interpose the suture thread therebetween are disposed at the ends of the pair of bent pieces, respectively.

3 Claims, 36 Drawing Sheets

SUTURE TOOL

BACKGROUND OF THE INVENTION

1. Technical Field

The present invention relates to a suture tool used in a suture instrument.

2. Background Art

Internal treatment of patients can be classified into surgical incision of the patient's body and oral or anal endoscopic treatment. The oral endoscopic treatment can be used to suture a perforation of the digestive canal. At this time, a suture tool having a suture thread extending from an anchor is inserted to the perforation in an oral endoscopic manner, punctures a tissue in the vicinity of the perforation with the suture tool housed in a puncture needle, and pushes up the anchor connected to the suture thread out of the puncture needle. By pulling out the puncture needle from the tissue and then tying two suture threads with the perforation interposed therebetween, the perforation is sutured (see U.S. patent application Ser. No. 11/238,016).

SUMMARY OF THE INVENTION

According to an aspect of the invention, there is provided a suture tool including an engaging member which is detained in a biological tissue, a suture thread which is drawn from the engaging member, and a fixing member which is penetrated by the suture thread and which restricts a looseness of the suture thread from the biological tissue anastomosed by the suture thread. Here, the fixing member includes: a base portion which has a thin and longitudinal plate shape and which has a through-hole through which the suture thread passes; and a pair of bent pieces of which ends are opposed to each other by bending both ends of the base portion toward the center thereof. Thick plate portions which are thick in an insertion direction of the suture thread and which interpose the suture thread therebetween are disposed at the ends of the pair of bent pieces, respectively.

DETAILED DESCRIPTION OF THE INVENTION

Figure 1:
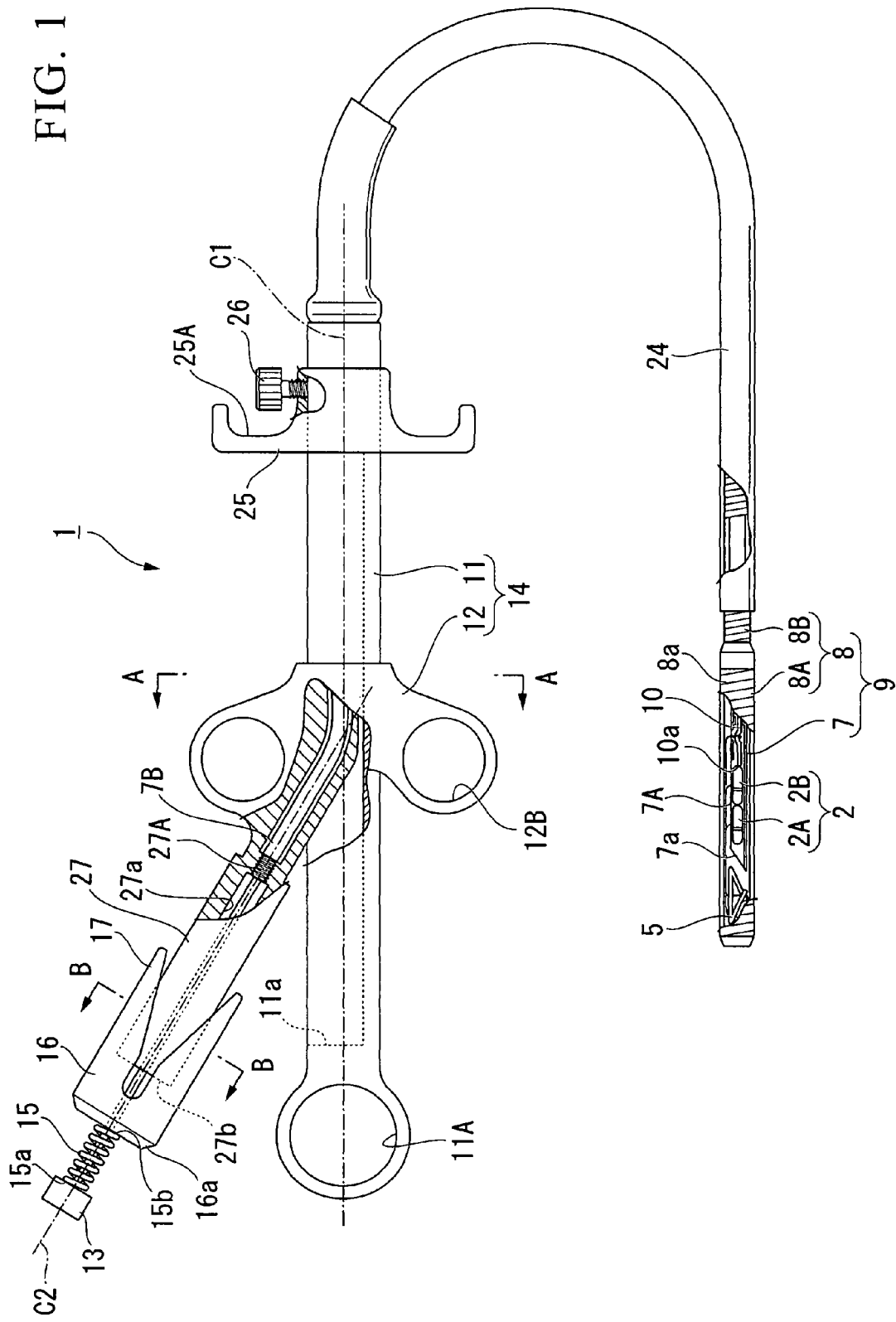
FIG. 1 is a diagram illustrating the entire appearance of a suture instrument in which a suture tool according to an embodiment of the invention is disposed.

Exemplary embodiments of the invention will be described in detail below. In the following description, like elements are denoted by like reference numerals and repeated description is omitted.

Figure 2:
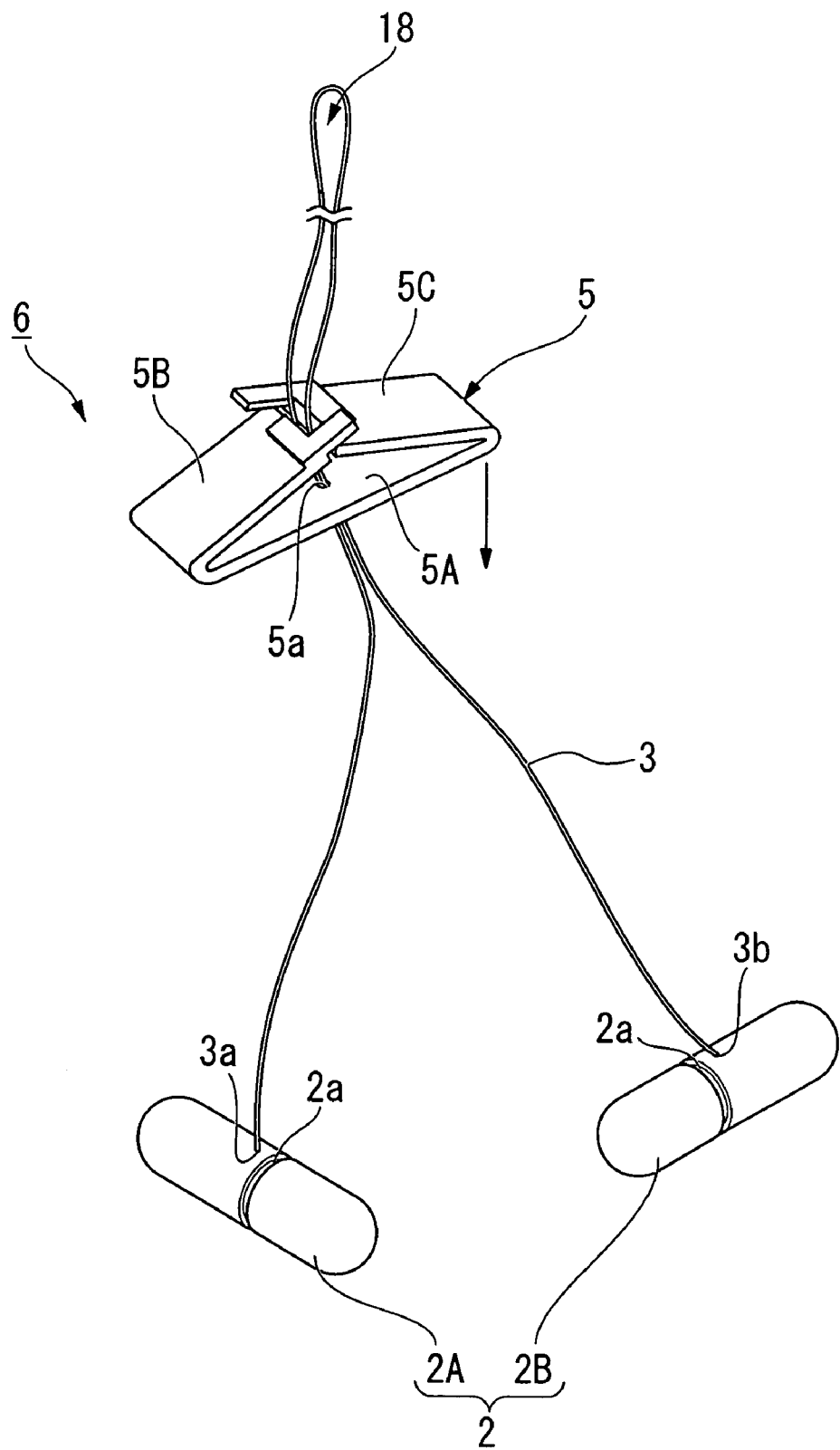
FIG. 2 is a diagram illustrating the entire appearance of the suture tool according to the embodiment of the invention.
Figure 3:
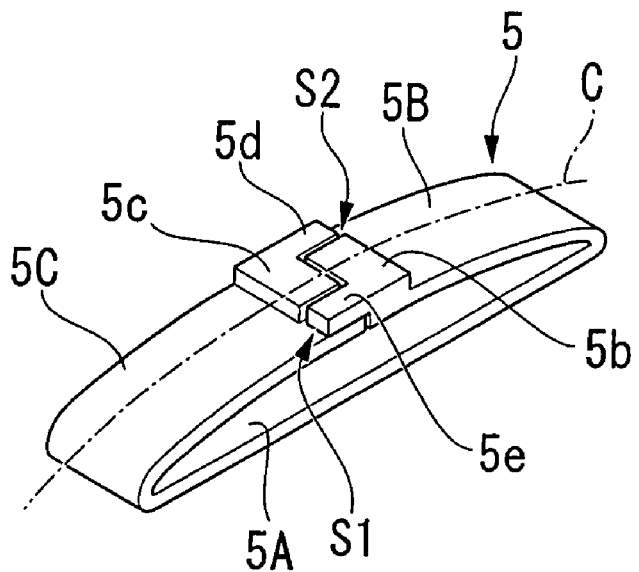
FIG. 3 is a perspective view illustrating a stopper of the suture tool.
Figure 4:
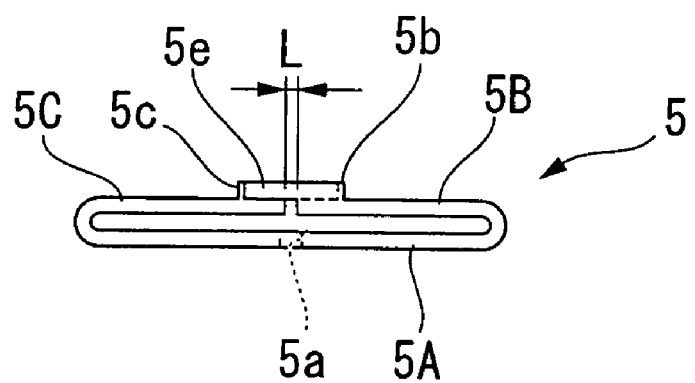
FIG. 4 is a side view of the stopper shown in FIG. 3.
Figure 5:
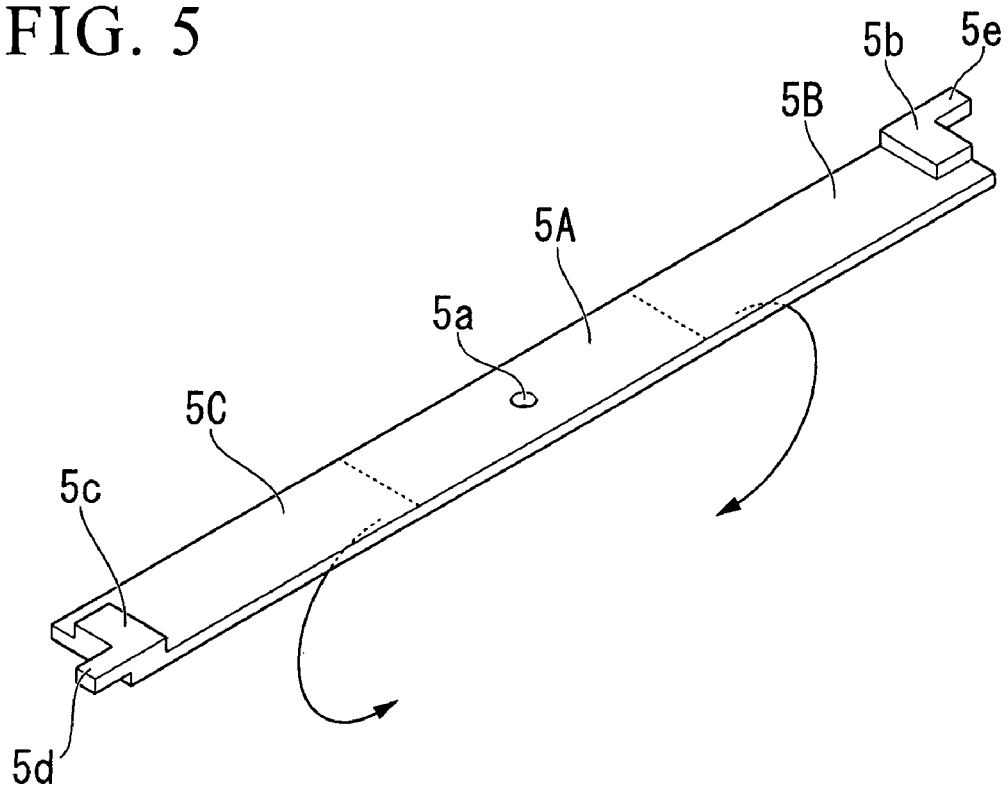
FIG. 5 is a development view illustrating the stopper shown in FIG. 3.

As shown in FIGS. 1 and 2, a suture tool 6 according to an embodiment of the invention has an anchor 2 locked to a biological tissue not shown, a suture thread 3 drawn out of the anchor 2, and a stopper 5 disposed on the suture thread 3, and is used along with a suture instrument 1, which includes a sheath 9 having a hollow puncture needle 7 which has a hard needle portion 7A having an opening 7a formed at the front end thereof and which houses the anchor 2 and an outer sheath 8 which houses the puncture needle 7 so as to advance and retreat; a pusher (wire) 10 which is disposed to advance and retreat in the puncture needle 7 and of which a proximal end extends to a proximal side in a state where a distal end 10a is in contact with the anchor 2; an operating section 14 having an operating section body 11 which extends from a base end of the outer sheath 8 and a needle slider (first operating section) 12 which is fixed to a base end of the puncture needle 7 and disposed in the operating section body 11 so as to advance and retreat; a pusher operating section (wire operating section, second operating section) 13 which is connected to a base end of the pusher 10 and disposed so as to advance and retreat relative to the operating section body 11; a spring member (resilient member) 15 which has a first end 15a and a second end 15b, the first end 15a of which is connected to the pusher operating section 13, and which expands and contracts between the second end 15b and the first end 15a; a movable stopper (movable member) 16 which is connected to the second end 15b and which is movable relative to the operating section 12; and a lock member (control member) 17 which is disposed in the movable stopper 16 and which switches the movable stopper 16 between a movable state and a fixed state relative to the operating section 12.

The anchor 2 of the suture tool 6 includes a first anchor 2A and a second anchor 2B. The anchors 2A and 2B have the same thin and longitudinal cylindrical shape and have a groove 2a in the circumferential direction at the center portion thereof. A first end 3a of the suture thread 3 extends from the vicinity of the groove 2a of the first anchor 2A. The suture thread 3 is bent back to form a loop 18 in which the pusher 10 is inserted, and a second end 3b is connected to the vicinity of the groove 2a of the second anchor 2B.

As shown in FIGS. 3 to 6, the stopper 5 has a base portion 5A and a pair of bent pieces 5B and 5C which are formed by bending back both ends of a band-shaped thin plate toward the center. The base portion 5A of the stopper 5 is provided with a through-hole 5a into which the suture thread 3 is inserted. The pair of bent pieces 5B and 5C are substantially parallel to the base portion 5A.

The front ends of the pair of bent pieces 5B and 5C are provided with thick plate portions 5b and 5c, which are thick in the insertion direction of the suture thread 3 and sandwich the suture thread 3 therebetween, at positions decentered in a direction separating each other from the center axis line C of the pair of bent pieces 5B and 5C. The distance L between the thick plate portions 5b and 5c is smaller than the diameter of the suture thread 3.

An engaging protrusion 5d protruding toward a gap S1 formed between a lateral edge of the bent piece 5B and the thick plate portion 5b due to the decentering is formed in the thick plate portion 5c disposed in the other bent piece 5C opposed to the bent piece 5B. Similarly, an engaging protrusion 5e protruding toward a gap S2 formed between a lateral edge of the bent piece 5C and the thick plate portion 5c is formed in the thick plate portion 5b disposed in the bent piece 5B.

Figure 6:
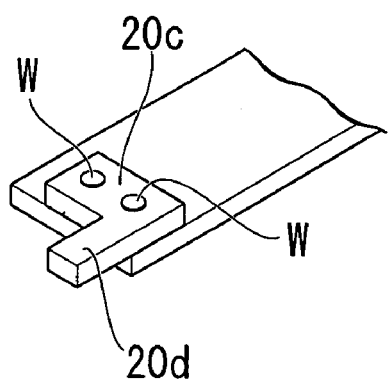
FIG. 6 is a partially enlarged view illustrating a modified example of the stopper shown in FIG. 3.

The stopper 5 is shaped by pressing portions other than the thick plate portions 5b and 5c of the band-shaped thin plate member with a thickness of 0.4 mm up to 0.2 mm. Thereafter, the portions having a predetermined length from both ends are bent back toward the center to form the base portion 5A and the pair of bent pieces 5B and 5C. Alternatively, as shown in FIG. 6, thick plate portions 20c and engaging protrusions 20d with a thickness of 0.4 mm may be secured at both ends of a band-shaped thin plate member with a thickness of 0.2 mm by means of caulking or welding W to form a stopper 20.

The puncture needle 7 has a tube-shaped proximal side member 7B of which a front end is connected to the needle portion 7A. The proximal side member 7B is formed of a soft flexible member. The proximal side member 7B is formed of an extruded tube of PEEK (poly etherether ketone) so as to endure an expanding and contracting load accompanied with the protruding and retracting of the puncture needle 7 relative to the outer sheath 8 and an expanding load due to the movement of the stopper 5 over the suture thread 3 accompanied with a tightening of a biological tissue.

Figure 7:
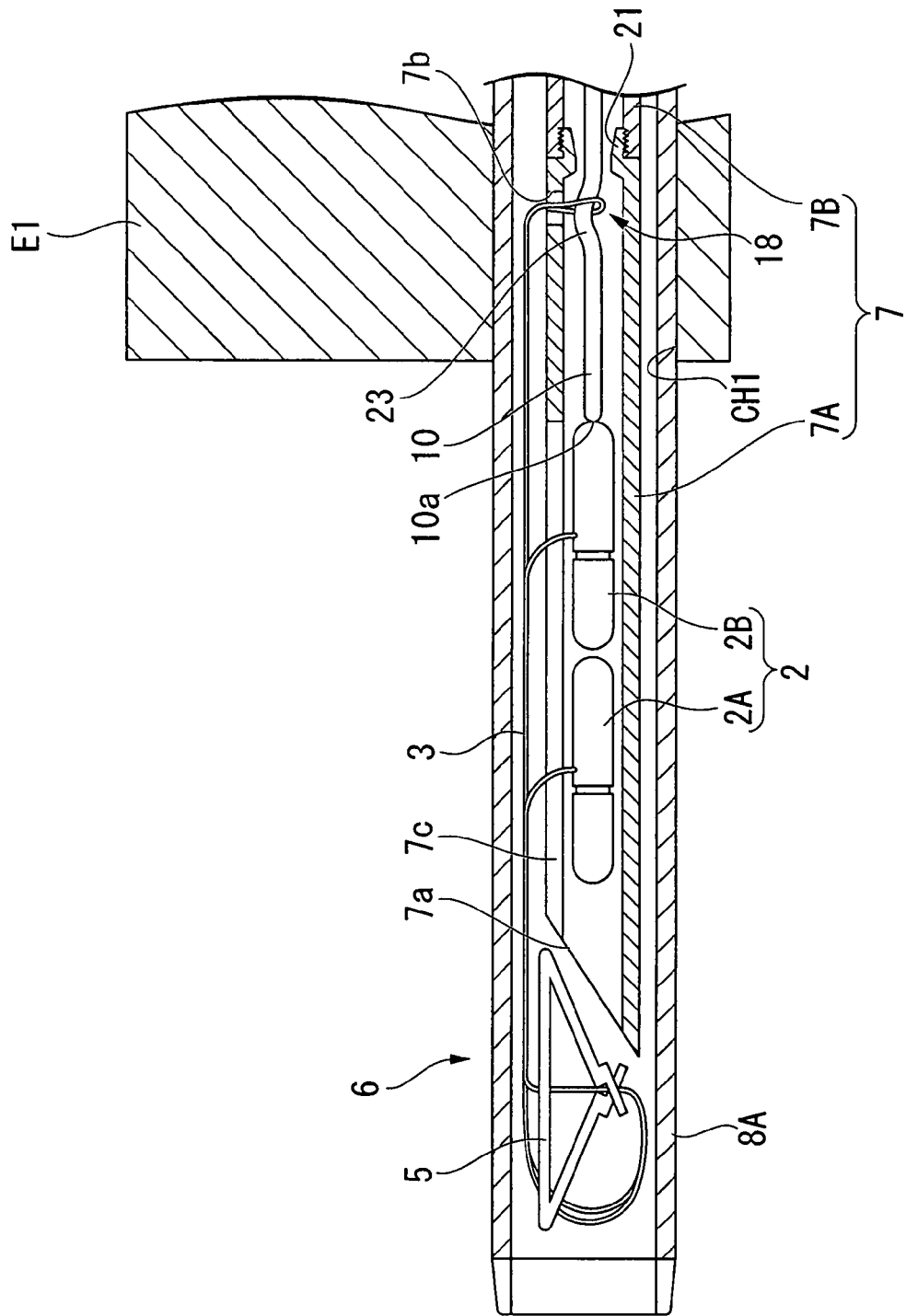
FIG. 7 is a partially enlarged sectional view of the suture instrument.
Figure 8:
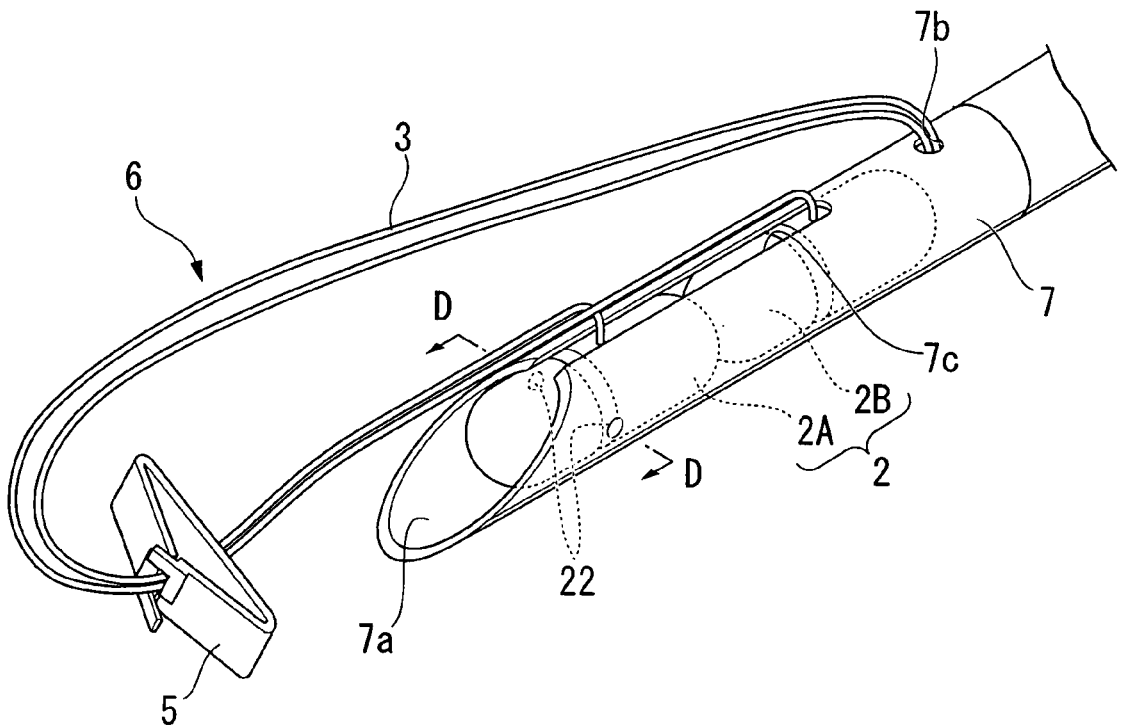
FIG. 8 is a partial perspective view of the suture instrument.
Figure 9:
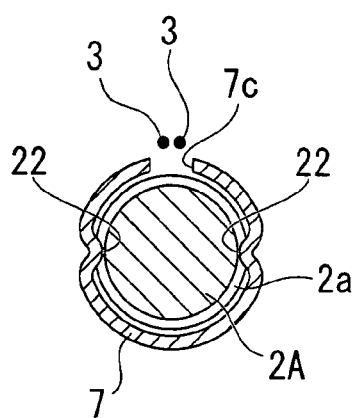
FIG. 9 is a cross-sectional view taken along line D-D of FIG. 8.

As shown in FIGS. 7 to 9, the puncture needle 7 is inserted into a channel CH1 of an endoscope insertion section EI to be described later along with the outer sheath 8. The opening 7a at the front end of the puncture needle 7 is inclined about the longitudinal direction of the puncture needle 7. An introduction hole 7b for introducing a loop 18 of the suture thread 3 into a cavity of the puncture needle 7 from the outside thereof is formed in a side surface of the puncture needle 7 closer to the proximal side than the front end position of the pusher 10. Specifically, the introduction hole 7b is disposed at a position apart from the opening 7a by the total length or more of the first anchor 2A and the second anchor 2B arranged in series. A slit 7c having sufficient width to pass the suture thread 3 therethrough is disposed from the opening 7a toward the introduction hole 7b.

A restriction member 21 for restricting the moving amount of the pusher 10 to the proximal side in the puncture needle 7 is disposed at a position closer to the proximal side than the introduction hole 7b of the puncture needle 7 so as to protrude inwardly in the diameter direction.

The restriction member 21 is disposed in the base end of the needle portion 7A which is closer to the proximal side than the introduction hole 7b of the puncture needle 7 so as to protrude inwardly in the diameter direction. In the restriction member 21, the slope close to the front end of the puncture needle 7 is steep and the slope close to the proximal side is gentle. A male screw portion is formed on the outer circumferential surface of the restriction member 21 and a female screw portion capable of engaging with the male screw portion is formed at the front end of the proximal side member 7B. Accordingly, the needle portion 7A and the proximal side member 7B are coupled to each other with sufficient strength to endure a high expanding and contracting load and with a simple structure by allowing them to engage with each other in a screwing manner.

The inner circumferential surface of the front side of the puncture needle 7 is provided with protrusions 22 engaging with the grooves 2a at the time of housing the first anchor 2A and the second anchor 2B.

The pusher 10 is made of a thin longitudinal wire. The pusher 10 is provided with an engaging portion 23 detachably engaging with the suture thread 3 drawn out of the slit 7c with the anchors 2 of the suture tool 6 housed in the puncture needle 7. The engaging portion 23 is formed by curving a part of the front side of the pusher 10.

The outer sheath 8 includes a front side sheath 8A which covers the front side of the puncture needle 7 having housed the suture tool 6 and a proximal side sheath 8B which is connected to the base end of the front side sheath 8A to cover the proximal side. The outer sheath 8 is constructed of densely wound metal wires 8a in a coil shape. The front side sheath 8A has an inner diameter larger than that of the proximal side sheath 8B so as to house the stopper 5 and the puncture needle 7.

The outer surface of the proximal side sheath 8B is covered with a resin tube 24. The resin tube 24 is closely fixed onto the metal wire 8a by means of a thermal contraction method. Alternatively, the resin tube 24 is formed by means of an extrusion molding method using a coil not shown as a core. A resin coating may be used instead of the resin tube 24.

Figure 10:
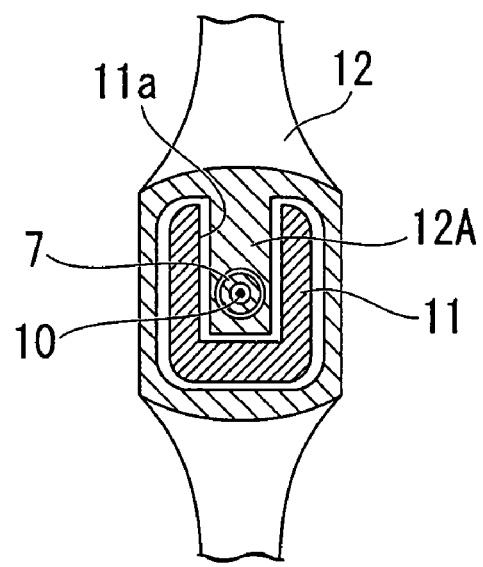
FIG. 10 is a cross-sectional view taken along line A-A of FIG. 1.
Figure 11:
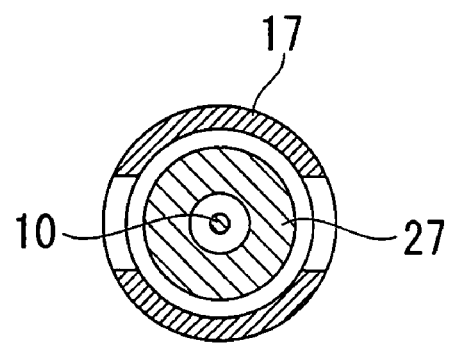
FIG. 11 is a cross-sectional view taken along line B-B of FIG. 1.

As shown in FIGS. 1, 10, and 11, a groove 11a having a U shape in the direction of the center axis C1 is formed in the operating section body 11 and a finger laying portion 11A is disposed in the base end of the operating section body 11. A control stopper 25 for restricting the movement of the needle slider 12 is disposed in the front side of the operating section body 11. The control stopper 25 is positioned in the operating section body 11 by the use of a fixing screw 26. The control stopper 25 is provided with a semi-circular finger laying portion 25A.

The needle slider 12 has a protruding member 12A engaging with the U-shaped groove 11a and engages with the operating section body 11 so as to advance and retreat. At the base end of the needle slider 12, a branch section 27 extending in the direction of a center axis C2 inclined about the center axis C1 is connected to the protruding member 12A. The needle slider 12 includes two finger laying portions 12B.

The base end portion of the branch section 27 is provided with a pusher through-hole 27a into which the base end of the pusher 10 is inserted. The front end of the pusher through-hole 27a is provided with a needle fixing portion 27A which is inserted into the base end of the proximal side member 7B of the puncture needle 7 and which is screwed similarly to the connection of the front end of the proximal side member 7B. The branch section 27 has a cylinder shape and is surrounded with a movable stopper 16 so as to advance and retreat.

The pusher operating section 13 is formed in a cylinder shape and is connected to the base end of the pusher 10.

The spring member 15 has a resilient force adjusted so that the moving distance of the pusher 10 corresponds to the length of one anchor 2 when it is compressed to the maximum. The resilient force is adjusted to be smaller than the frictional force between the pusher 10 and the puncture needle 7.

The movable stopper 16 is formed in a bottomed cylindrical shape and is externally inserted to be slidable in a state where a bottom portion 16a is apart by a predetermined distance from the base end 27b of the branch section 27. A second end 15b of the spring member 15 is connected to the bottom portion 16a.

The lock member 17 protrudes from the movable stopper 16 in the longitudinal direction of the pusher operating section 13 and is resiliently deformed in a direction in which the diameter of the movable stopper 16 decreases.

Figure 12:
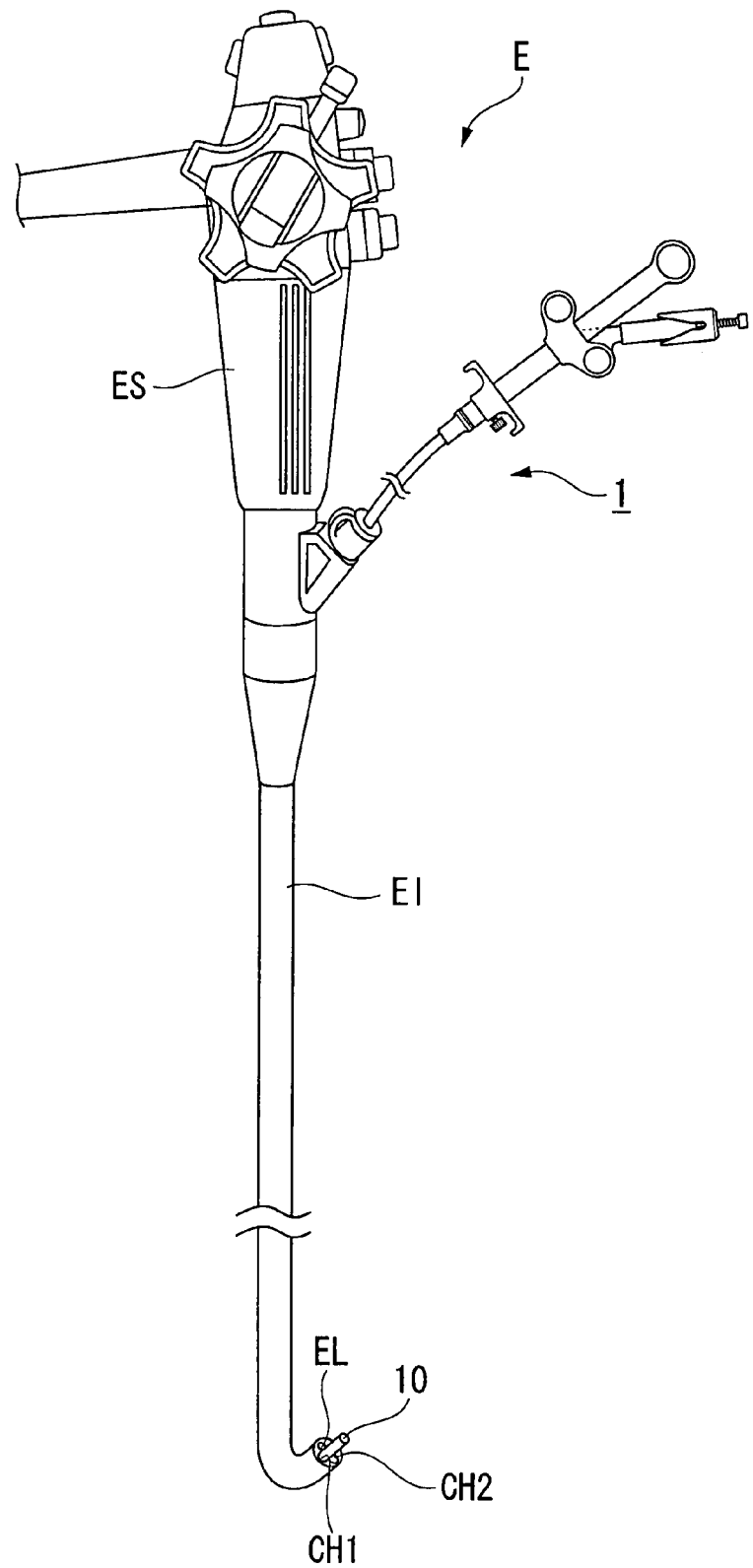
FIG. 12 is a diagram illustrating the entire appearance of an endoscope used along with the suture instrument.

The suture instrument 1 is used along with an endoscope E, as shown in FIG. 12. The endoscope E includes an endoscope operating section ES operated by an operator and a flexible endoscope insertion section EI extending from the endoscope operating section ES. The endoscope insertion section EI is provided with channels CH1 and CH2 into which the suture instrument 1 and the like are inserted and which are opened at the front end of the endoscope insertion section EI. A lighting optical system EL is disposed in the front end of the endoscope insertion section EI.

Next, operations of the suture instrument 1 and the suture tool 6 are described along with a suturing method with reference to FIGS. 13 to 43. The stomach is shown as an example of a hollow organ.

Figure 13:
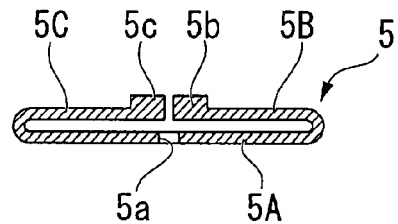
FIG. 13 is an explanatory diagram illustrating a state where a suture thread is inserted into the stopper shown in FIG. 3.
Figure 14:
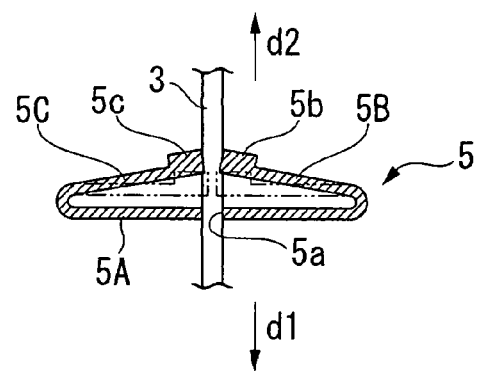
FIG. 14 is an explanatory diagram illustrating a state where a suture thread is inserted into the stopper shown in FIG. 3.

First, in the stopper 5 shown in FIG. 13, as shown in FIG. 14, the suture thread 3 is inserted into the through-hole 5a of the base portion 5A and passes through while the pair of bent pieces 5B and 5C is deformed in a direction in which the thick plate portions 5b and 5c are apart from each other. At this time, when the suture thread 3 is drawn in a direction d1 of the base portion 5A, the thick plate portions 5b and 5c also move in the direction d1 and the distance between the thick plate portions 5b and 5c decreases to tightly fasten and lock the suture thread 3, thereby restricting the movement of the suture thread 3.

That is, when a force acts on the suture thread 3 in a direction in which the anchors 2 are separated from the stopper 5, the pair of bent pieces 5B and 5C are moved to be closer to each other, thereby locking the movement of the suture thread 3. That is, even when an anastomosis object to be anastomosed by the stopper 5 and the anchors 2 pushes the stopper 5 in a direction d2 toward the other end of the suture thread 3, the thick plate portions 5b and 5c tightly fasten the suture thread 3 and lock the position of the stopper 5 relative to the suture thread 3. As a result, the stopper 5 is not moved in the direction d2.

Figure 15:
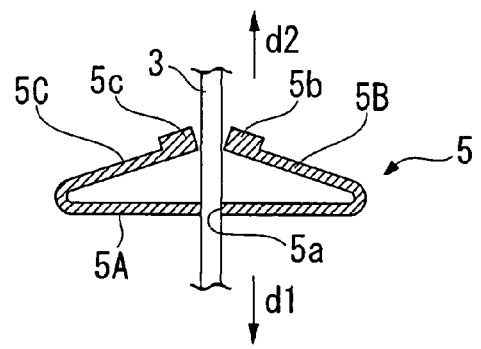
FIG. 15 is an explanatory diagram illustrating a state where a suture thread is inserted into the stopper shown in FIG. 3.

On the other hand, as shown in FIG. 15, when the stopper 5 is moved to be closer to the anchors 2, that is, when the suture thread 3 is drawn in the direction d2 opposite to the base portion 5A, the thick plate portions 5b and 5c also move in the direction d2 (in a direction in which they are separated from each other), thereby releasing the fastening to the suture thread 3. That is, the movement of the suture thread 3 is allowed in the direction in which the anchors 2 and the stopper 5 are closer to each other. That is, when the stopper 5 is pressed to the anastomosis object, that is, when the stopper 5 is moved in the direction d1 of one end of the suture thread 3, the thick plate portions 5*b* and 5*c* are opened and the fastening of the thick plate portions 5*b* and 5*c* to the suture thread 3 is released.

Figure 16:
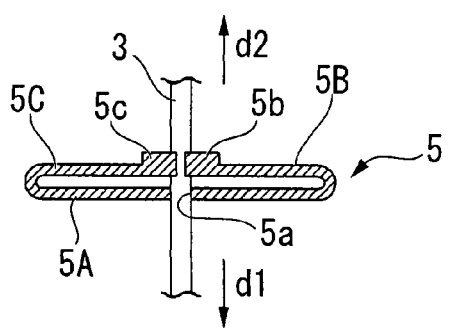
FIG. 16 is an explanatory diagram illustrating a state where a suture thread is inserted into the stopper shown in FIG. 3.

As shown in FIG. 16, the stopper 5 is compulsorily moved in the direction d2 by means of the pressure from the anastomosis object. At this time, the base portion 5A of the stopper 5 and the pair of bent portions 5B and 5C of the stopper 5 are substantially parallel to each other. Since this state is similar to the molded state, the bending stress hardly occurs in the pair of bent pieces 5B and 5C. Accordingly, the fastening force on the suture thread 3 is maintained without moving relative to the anastomosis object.

Figure 17:
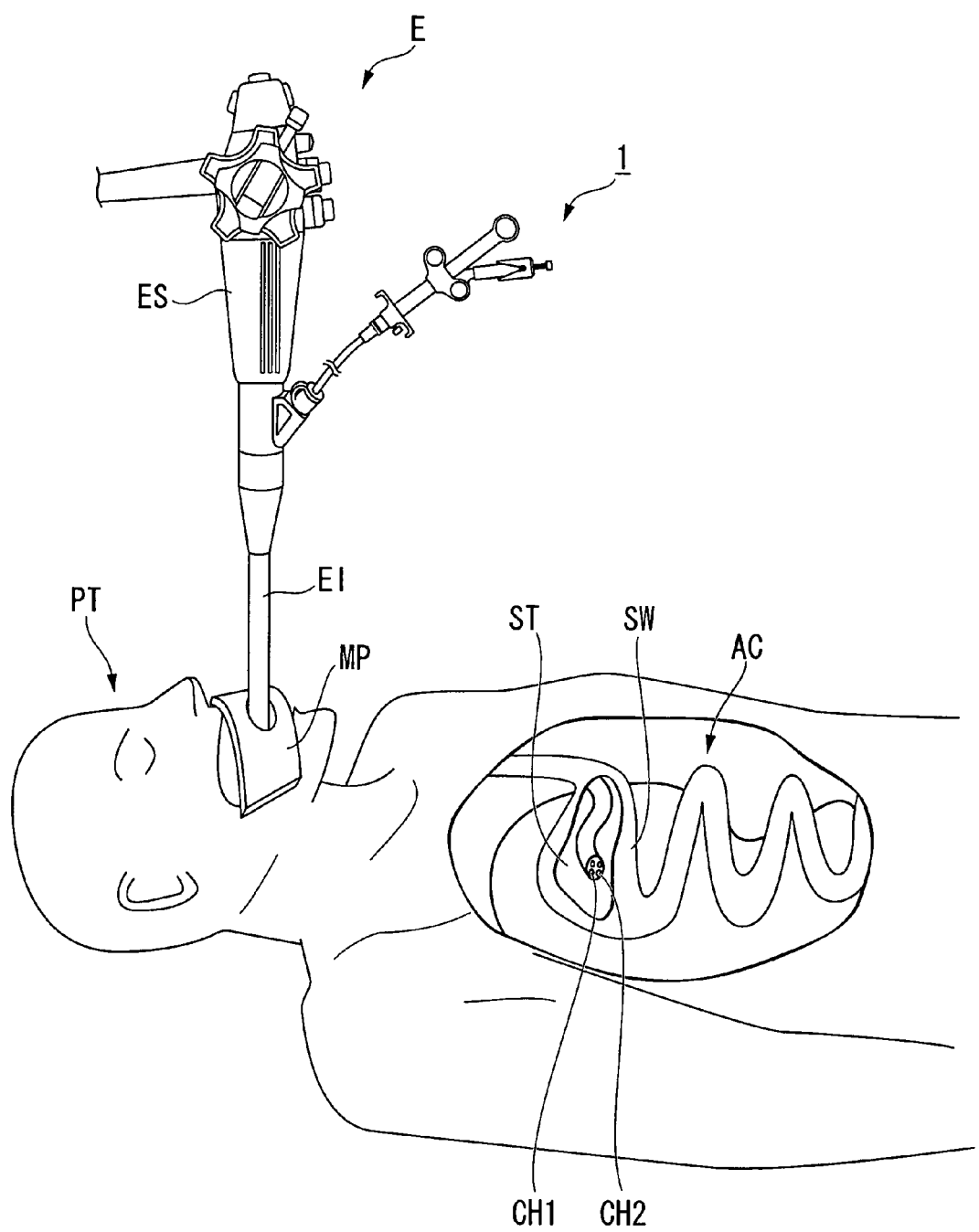
FIG. 17 is an explanatory diagram illustrating an operation of the suture instrument.
Figure 18:
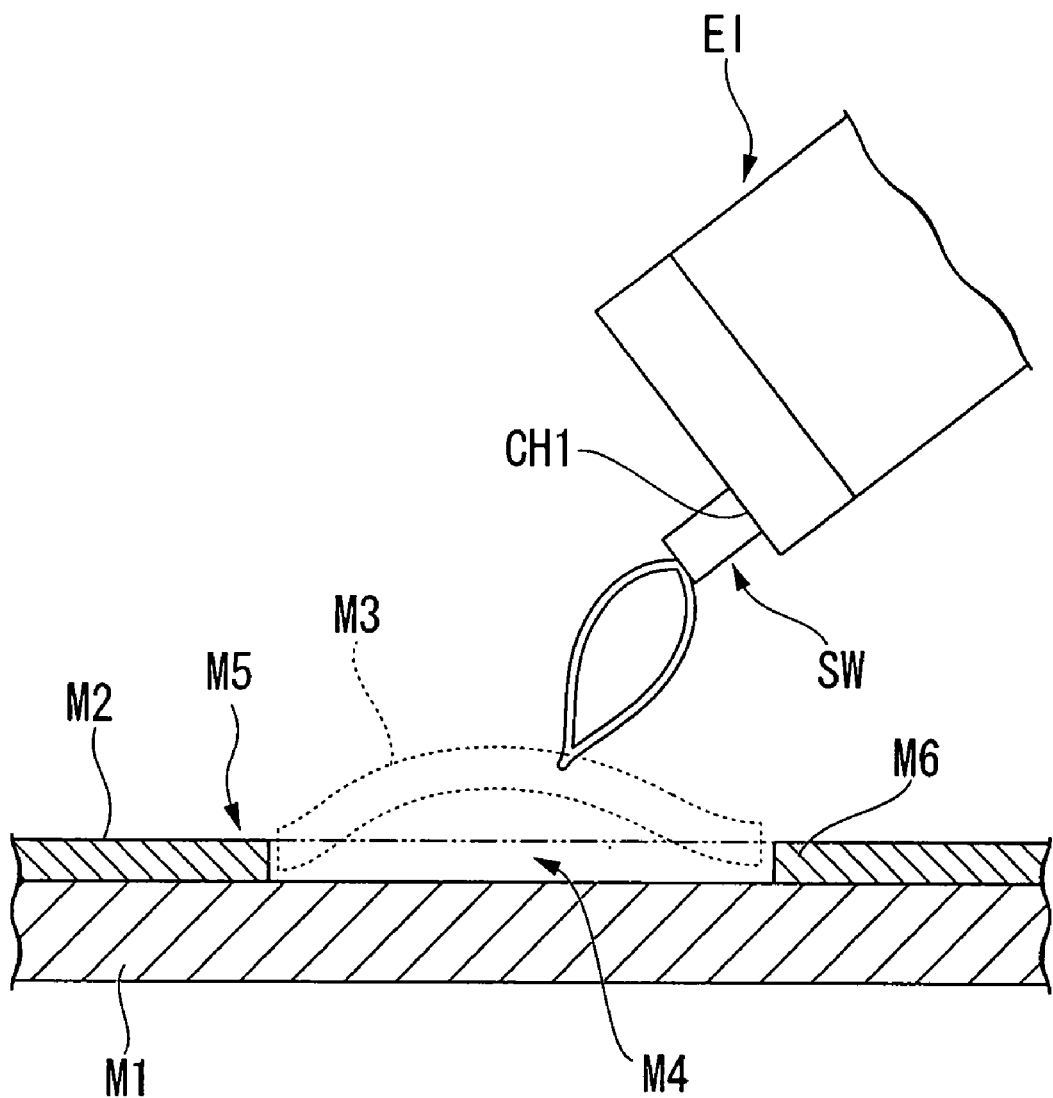
FIG. 18 is an explanatory diagram illustrating an operation of the suture instrument.

Next, as shown in FIG. 17, the endoscope insertion section EI is inserted into the mouth of a patient PT wearing a mouthpiece MP and the front end of the endoscope insertion section EI is curved. As shown in FIG. 18, an incising treatment instrument SW such as a snare is inserted into the channel CH1 of the endoscope insertion section EI to cut off a mucous membrane M3 including a pathological lesion.

Figure 19:
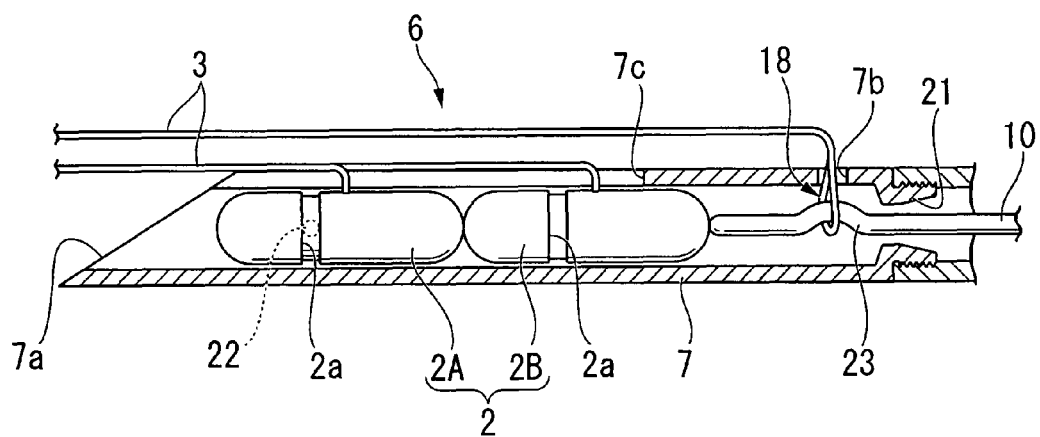
FIG. 19 is an explanatory diagram illustrating an operation of the suture instrument.

On the other hand, as shown in FIG. 19, the first anchor 2A and the second anchor 2B of the suture tool 6 are housed in series in the puncture needle 7 and the protrusion 22 is allowed to engage with the groove 2*a* of the first anchor 2A. The suture thread 3 is allowed to protrude from the slit 7*c* and the loop 18 is introduced again into the puncture needle 7 from the introduction hole 7*b*. The pusher 10 is allowed to be inserted into the loop 18 to engage with the engaging portion 23, thereby maintaining the stopper 5 in a state where it is housed in the puncture needle 7.

After cutting off the mucous membrane M3, the suture instrument 1 is inserted into the channel CH1 instead of the incising treatment instrument SW and the front end of the outer sheath 8 is allowed to protrude from the front end of the channel CH1.

Figure 20:
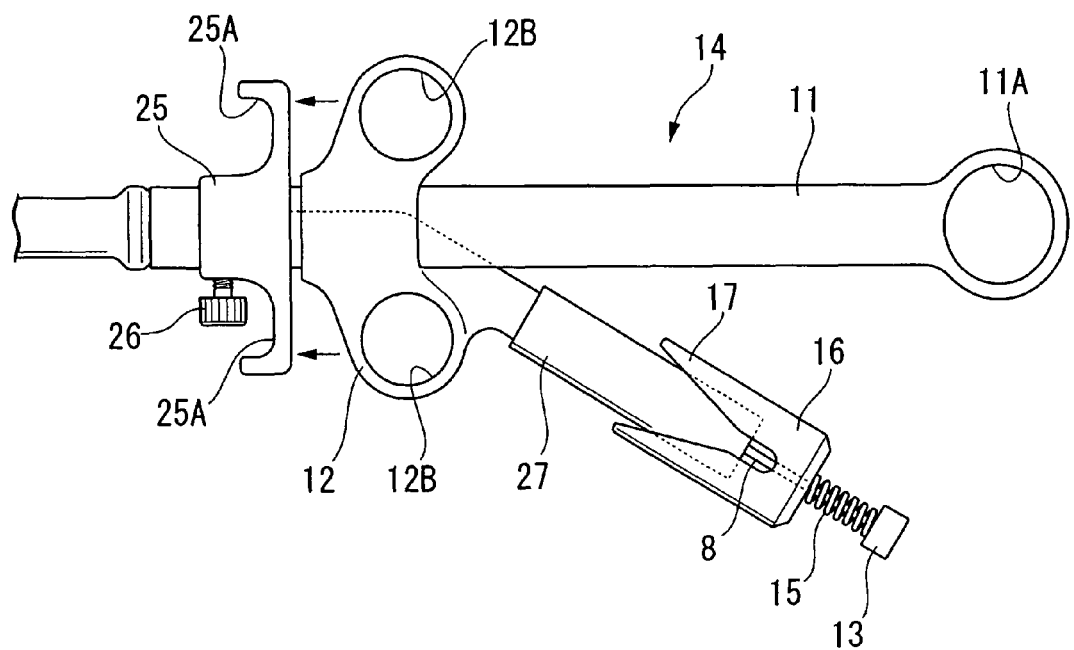
FIG. 20 is an explanatory diagram illustrating an operation of the suture instrument.
Figure 21:
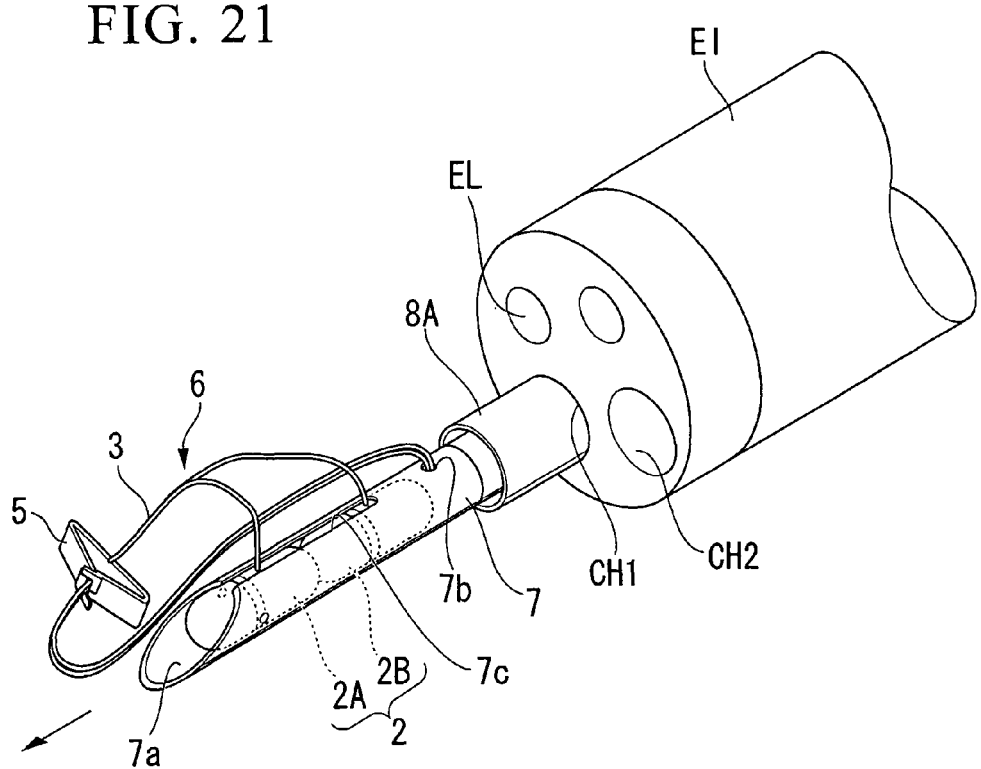
FIG. 21 is an explanatory diagram illustrating an operation of the suture instrument.

In this state, as shown in FIG. 20, the needle slider 12 is allowed to advance relative to the operating section body 11 and as shown in FIG. 21, the puncture needle 7 is allowed to protrude from the outer sheath 8. At this time, the needle slider 12 is moved forward by means of an operation of passing a thumb through the finger laying portion 11A, passing one of an index finger, a middle finger, and a ring finger through the finger laying portion 12B, and opening both fingers. Alternatively, the needle slider 12 may be moved forward by means of an operation of passing a thumb through the finger laying portion 12B, laying one of an index finger, a middle finger, and a ring finger on the semi-circular finger laying portion 25A, and closing both fingers. Since the closing operation can allow a more minute adjustment than the opening operation and thus can apply a force more conveniently, the protruding amount from the outer sheath 8 and the speed of the puncture needle 7 can be more easily controlled.

Figure 22:
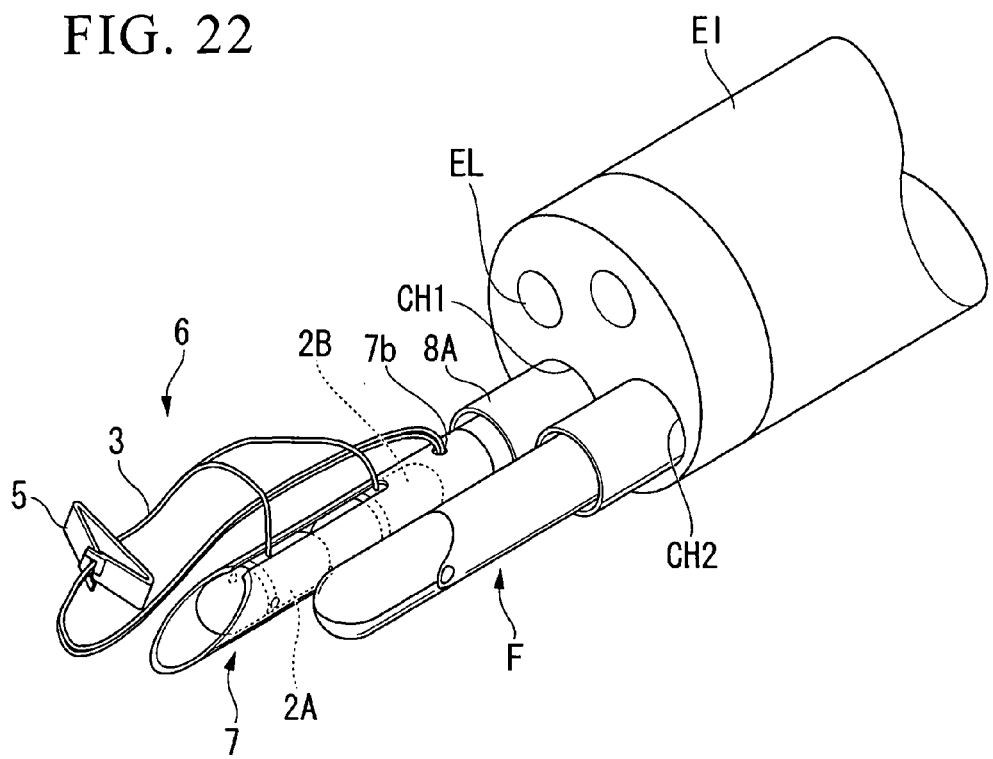
FIG. 22 is an explanatory diagram illustrating an operation of the suture instrument.
Figure 23:
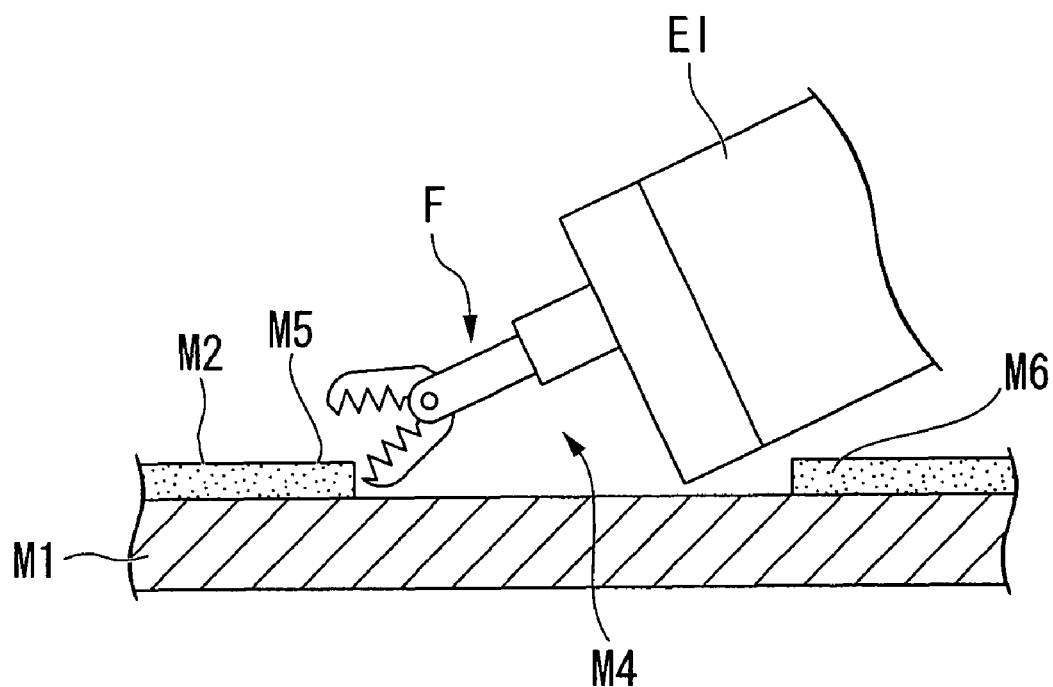
FIG. 23 is an explanatory diagram illustrating an operation of the suture instrument.

Next, as shown in FIG. 22, a forceps F is inserted into the channel CH2 and is allowed to protrude from the front end of the channel CH2, grasps a distal cut end M5 of a mucous-membrane lost portion M4 and pulls and holds up the distal cut end M5 in a direction apart from the mucous-membrane lost portion M4.

Figure 24:
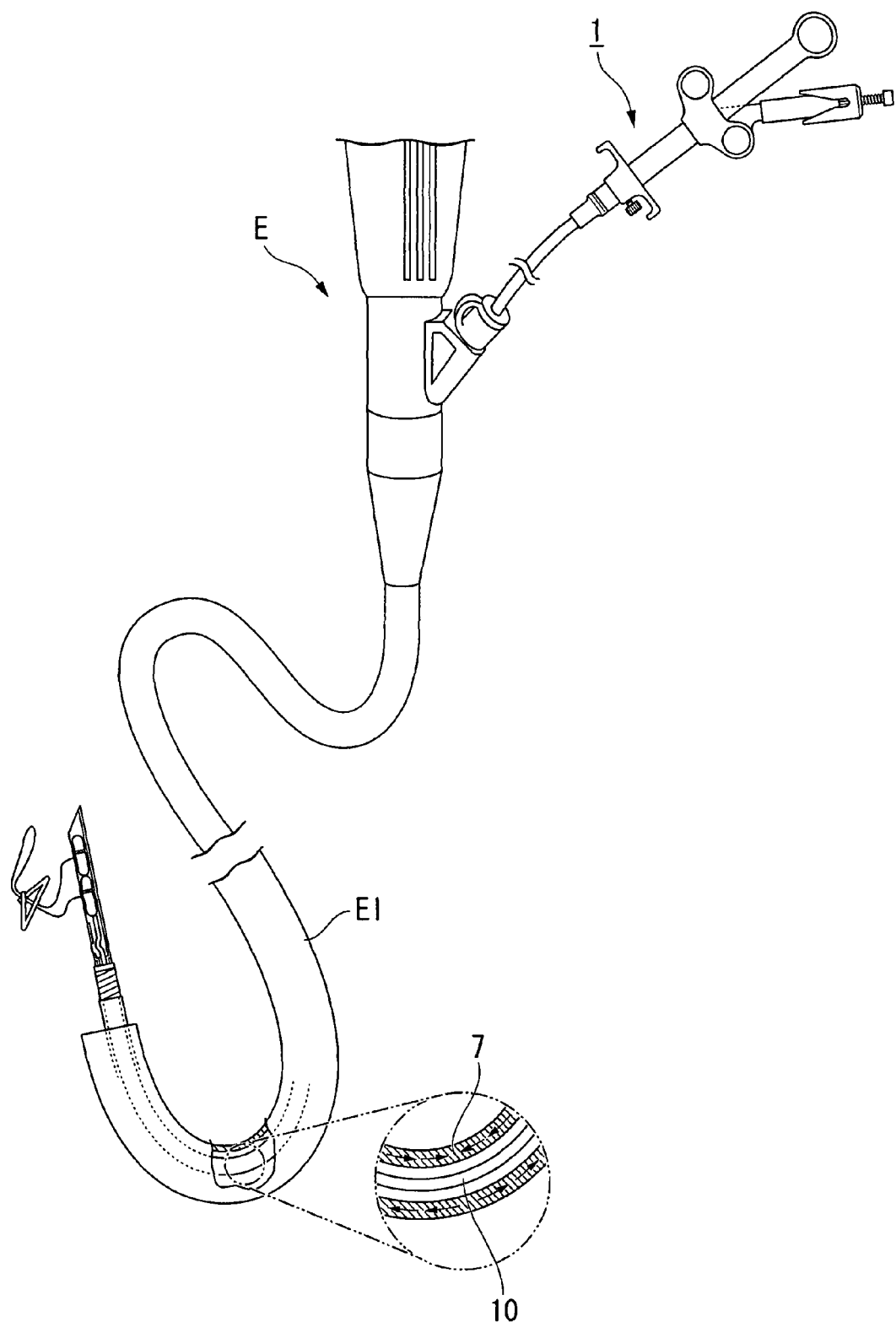
FIG. 24 is an explanatory diagram illustrating an operation of the suture instrument.

In this state, as shown in FIG. 24, the endoscope insertion section EI is curved to define the puncture direction of the puncture needle 7. At this time, since the proximal side member 7B of the puncture needle 7 is formed of a soft tube, the outer portion of the proximal side member 7B respect to the pusher 10 been as an axis expands in the curved direction. On the other hand, since the pusher 10 is a wire having a high rigidity and a small diameter, the pusher 10 does not expand with the curving operation. Accordingly, the engaging portion 23 of the pusher 10 engages with the restriction member 21 of the puncture needle 7 and thus the pusher operating section 13 is relatively drawn toward the branch section 27 along with the movable stopper 16.

Figure 25:
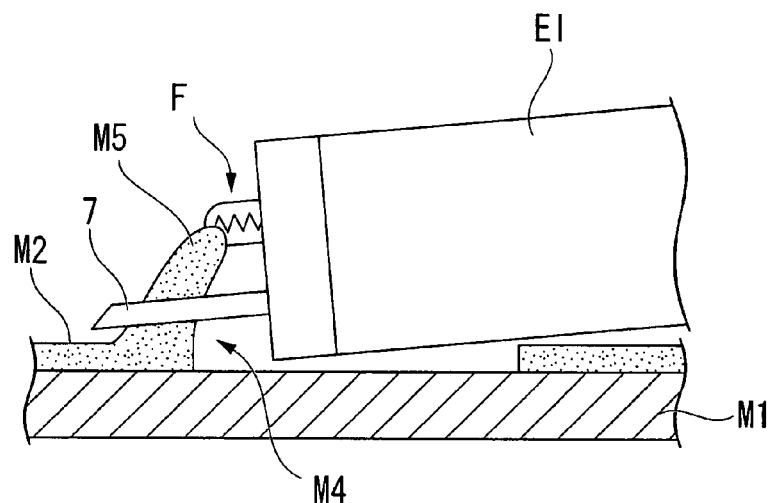
FIG. 25 is an explanatory diagram illustrating an operation of the suture instrument.

Thereafter, the needle slider 12 is allowed to advance relative to the operating section body 11 until coming in contact with the control stopper 25 so as to allow the puncture needle 7 to protrude from the front end of the outer sheath 8. In this way, as shown in FIG. 25, by allowing the entire suture instrument 1 or the endoscope insertion section EI to advance, the puncture needle 7 is allowed to pass through the held-up mucous membrane M5 by means of operations of the forceps F and the endoscope.

Figure 26:
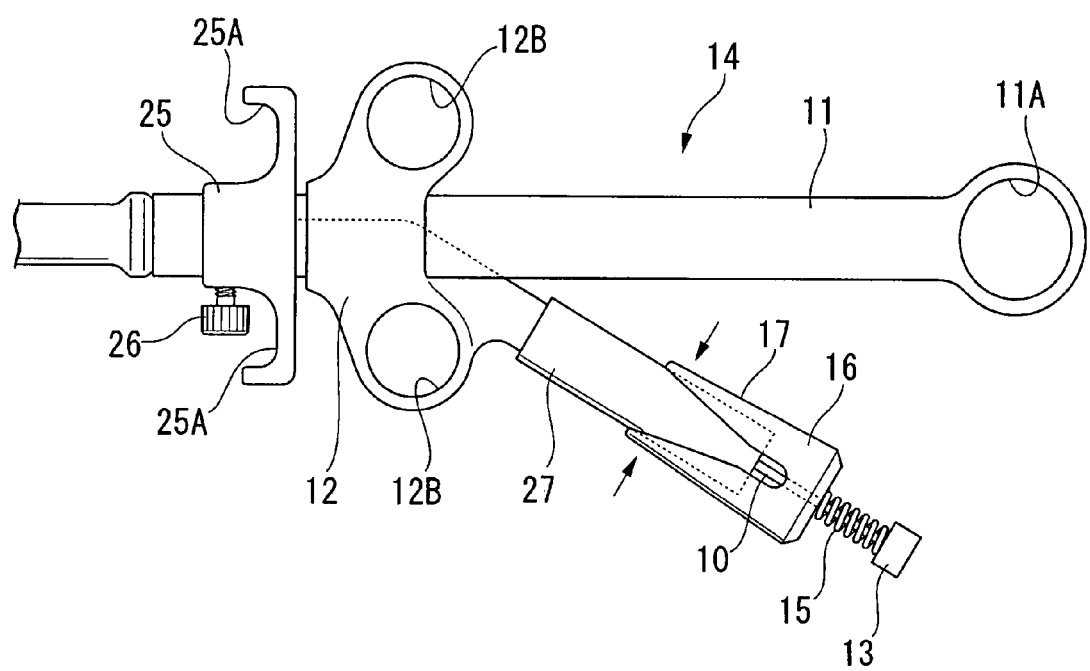
FIG. 26 is an explanatory diagram illustrating an operation of the suture instrument.
Figure 27:
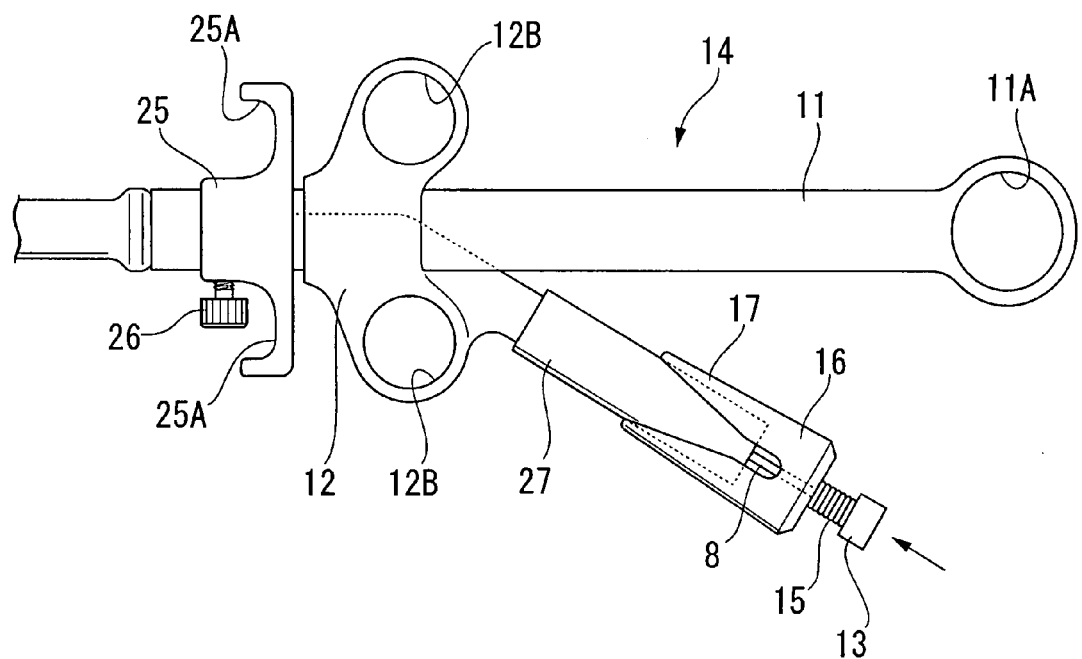
FIG. 27 is an explanatory diagram illustrating an operation of the suture instrument.
Figure 28:
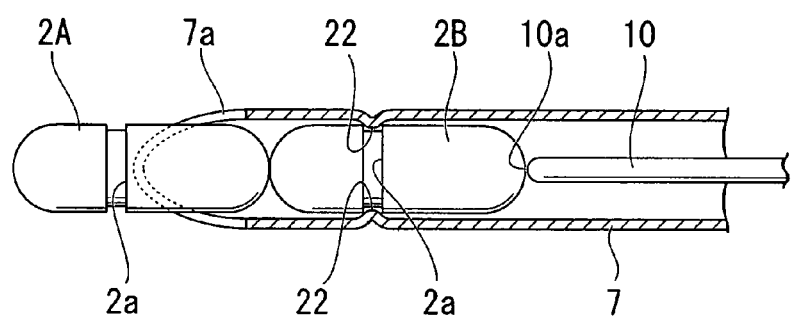
FIG. 28 is an explanatory diagram illustrating an operation of the suture instrument.

Next, as shown in FIG. 26, the movable stopper 16 and the branch section 27 are fixed to each other by grasping the lock member 17 of the movable stopper 16 along with the branch section 27. As shown in FIG. 27, the spring member 15 is compressed by moving the pusher operating section 13 toward the front end. At this time, the pusher 10 moves relative to the puncture needle 7 by the length of one anchor. Accordingly, the protrusion 22 and the groove 2*a* of the first anchor 2A are disengaged from each other and thus the second anchor 2B advances, as shown in FIG. 28, thereby extruding the first anchor 2A in a surface contact state toward the front end of the puncture needle 7. Then, the groove 2*a* of the second anchor 2B newly engages with the protrusion 22. As a result, the first anchor 2A drops to the rear side of the mucous membrane M5. When the puncture needle 7 is pulled out of the mucous membrane M5, the suture thread 3 passes through the mucous membrane M5 and the first anchor 2A is detained in the distal side of the mucous-membrane lost portion M4.

Figure 29:
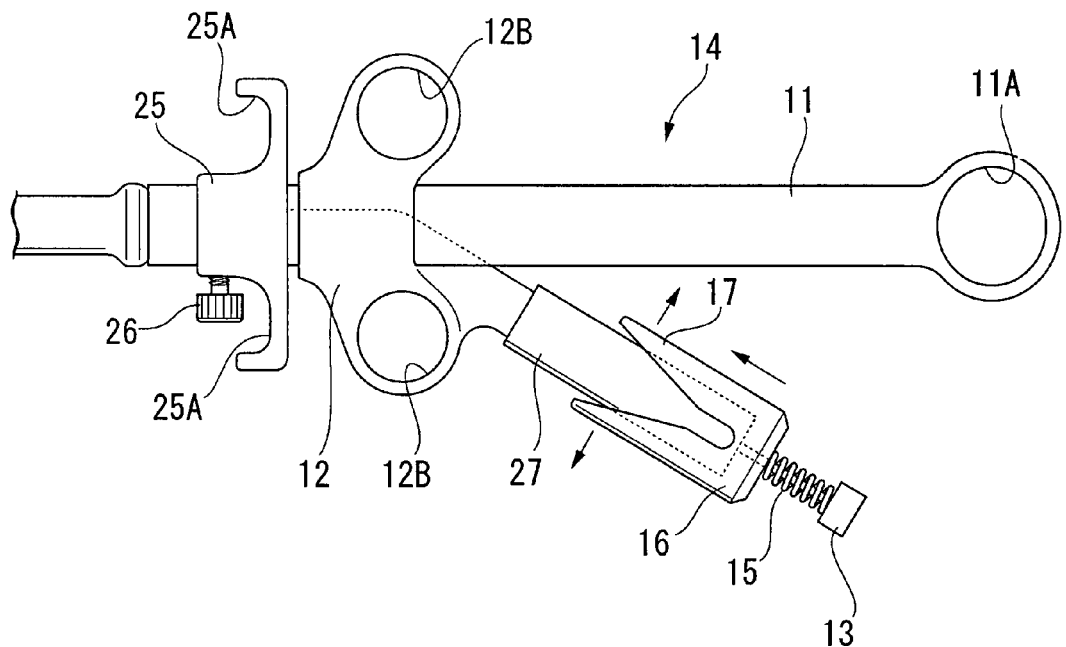
FIG. 29 is an explanatory diagram illustrating an operation of the suture instrument.

Subsequently, the lock member 17 is taken off and thus the movable stopper 16 is restored to the original shape. Here, the resilient restoring force of the spring member 15 is set smaller than the frictional force generated over the entire length between the pusher 10 and the puncture needle 7. Accordingly, while the spring member 15 is restored to the original length in a state where the pusher 10 and the puncture needle 7 are not relatively moved, the movable stopper 16 advances relative to the branch section 27, as shown in FIG. 29.

Figure 30:
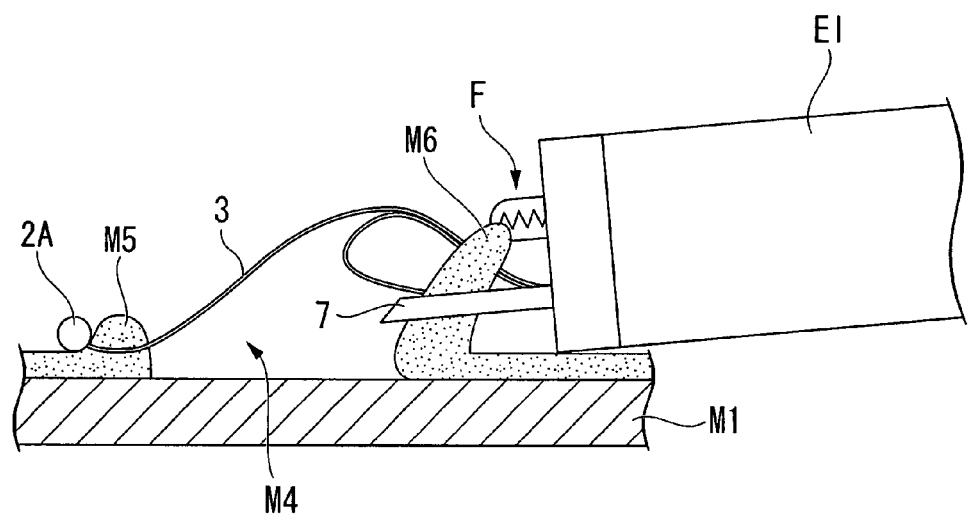
FIG. 30 is an explanatory diagram illustrating an operation of the suture instrument.

Next, the front end of the endoscope insertion section EI is moved to the place where the second anchor 2B should be detained. Similarly to the first anchor 2A, as shown in FIG. 30, the end portion of a mucous membrane M6 which is substantially symmetric with the mucous membrane M5 with the mucous-membrane lost portion M4 interposed therebetween is grasped and held up by the forceps F. By allowing the entire suture instrument 1 or the endoscope insertion section EI to advance again with the puncture needle 7 protruding from the front end of the outer sheath 8, the puncture needle 7 passes through the held-up mucous membrane M6.

Figure 31:
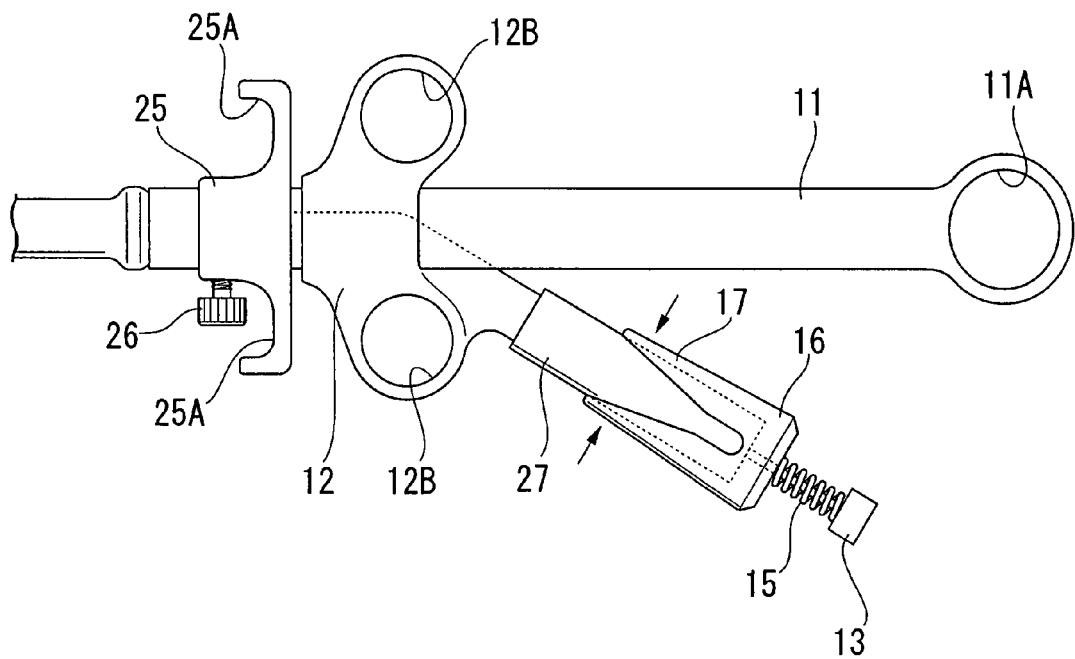
FIG. 31 is an explanatory diagram illustrating an operation of the suture instrument.
Figure 32:
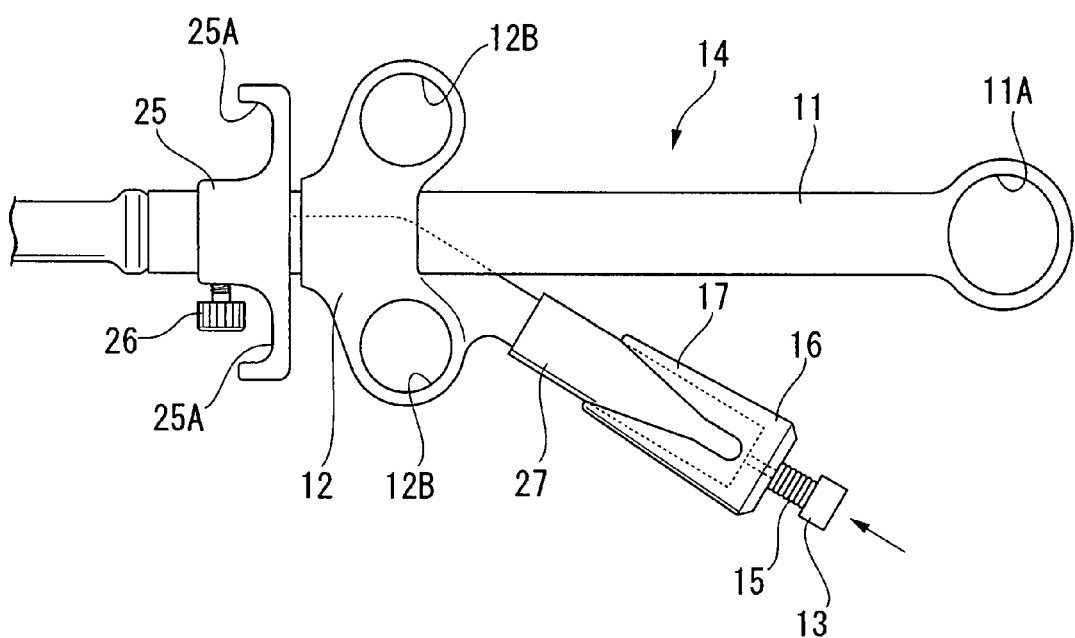
FIG. 32 is an explanatory diagram illustrating an operation of the suture instrument.
Figure 33:
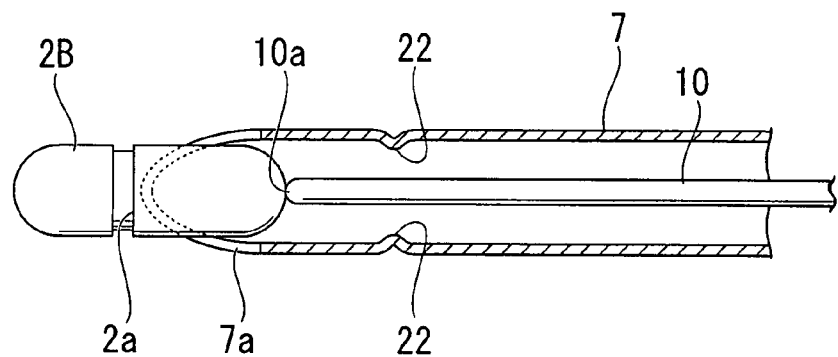
FIG. 33 is an explanatory diagram illustrating an operation of the suture instrument.
Figure 34:
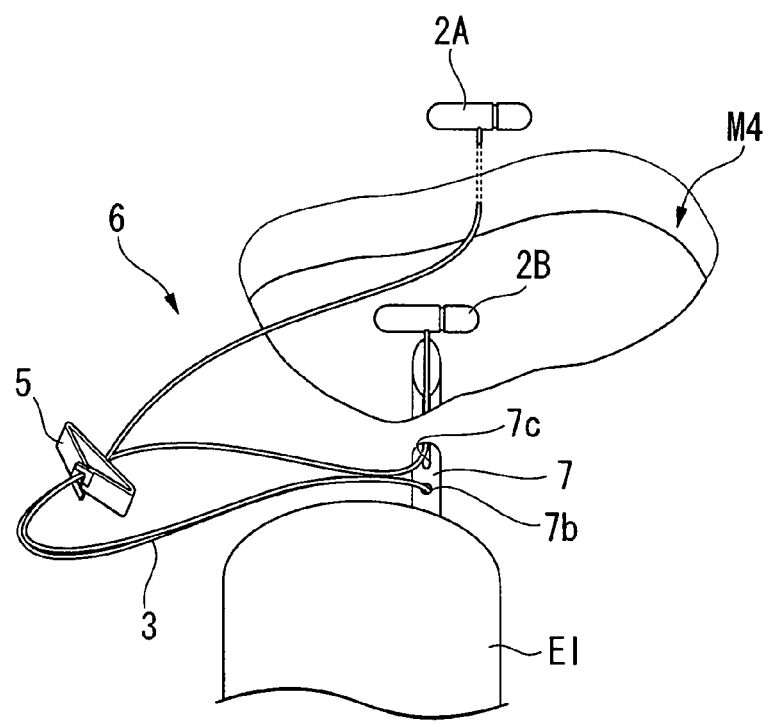
FIG. 34 is an explanatory diagram illustrating an operation of the suture instrument.

Here, as shown in FIG. 31, the lock member 17 is grasped and deformed again to come in contact with the branch section 27. As shown in FIG. 32, the pusher operating section 13 is moved relative to the movable stopper 16 to compress the spring member 15. Accordingly, as shown in FIG. 33, the protrusion 22 and the groove 2*a* of the second anchor 2B are disengaged from each other and thus the second anchor 2B is discharged to the rear side of the mucous membrane M6. When the puncture needle 7 is pulled out of the mucous membrane M6, the suture thread 3 penetrates the mucous membrane M6 and the second anchor 2B is detained in the proximal side of the mucous-membrane lost portion M4, as shown in FIG. 34.

Figure 35:
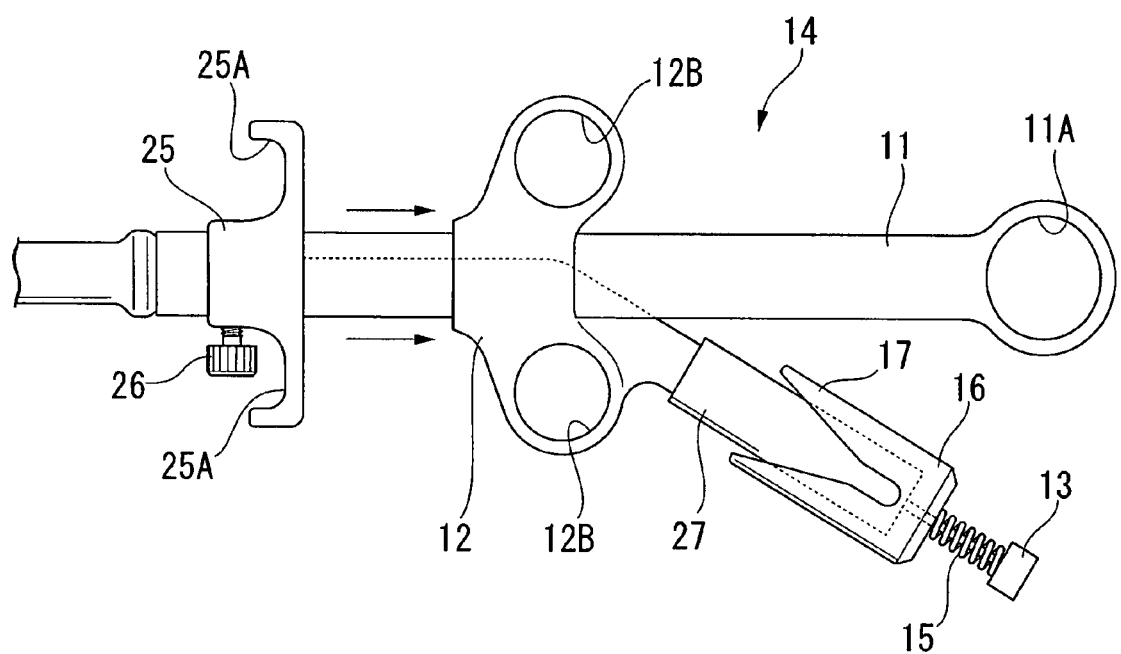
FIG. 35 is an explanatory diagram illustrating an operation of the suture instrument.
Figure 36:
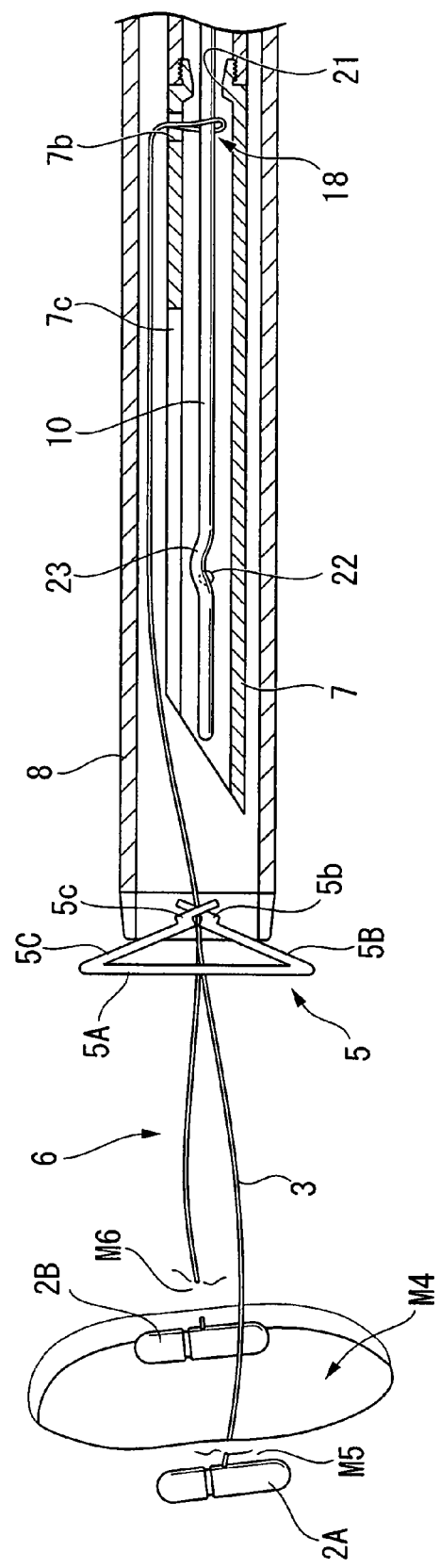
FIG. 36 is an explanatory diagram illustrating an operation of the suture instrument.
Figure 37:
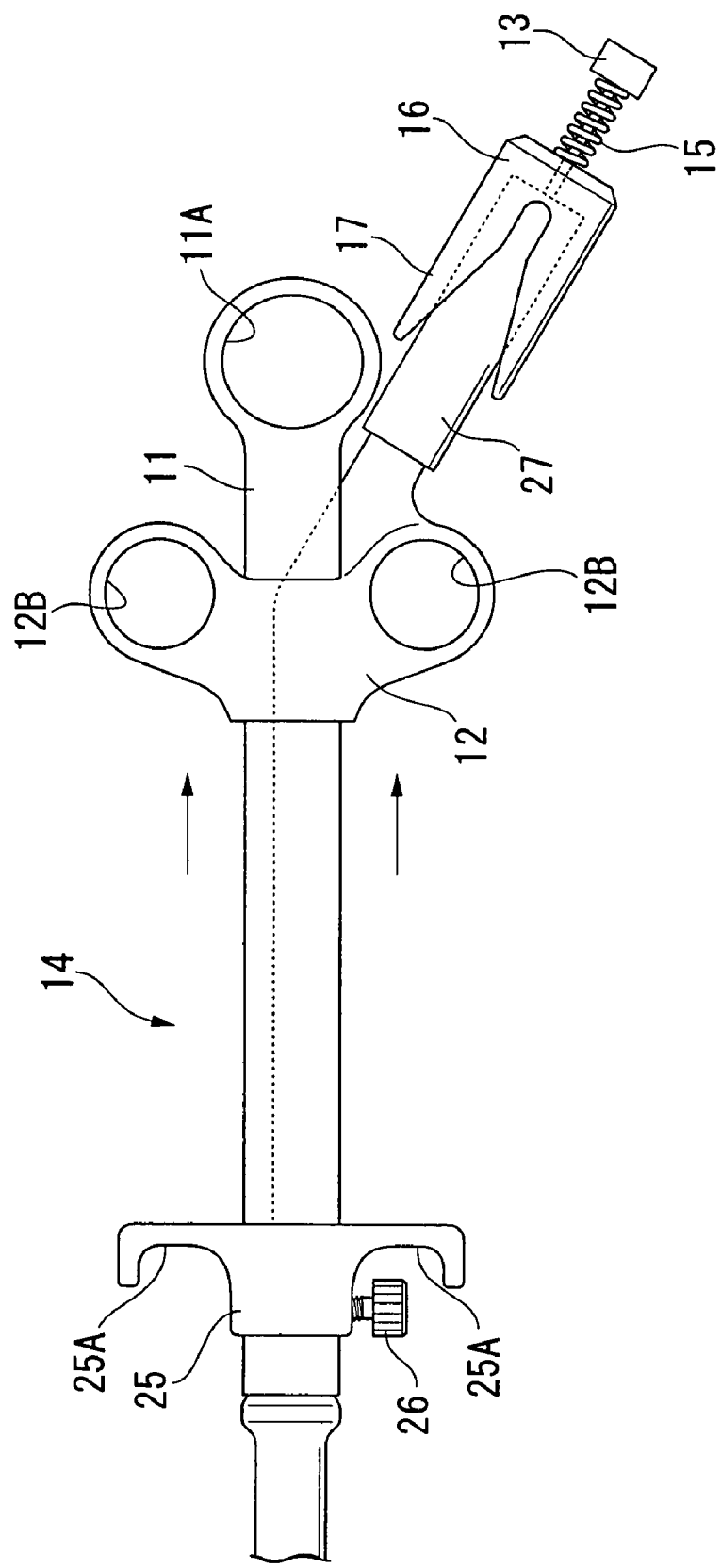
FIG. 37 is an explanatory diagram illustrating an operation of the suture instrument.
Figure 38:
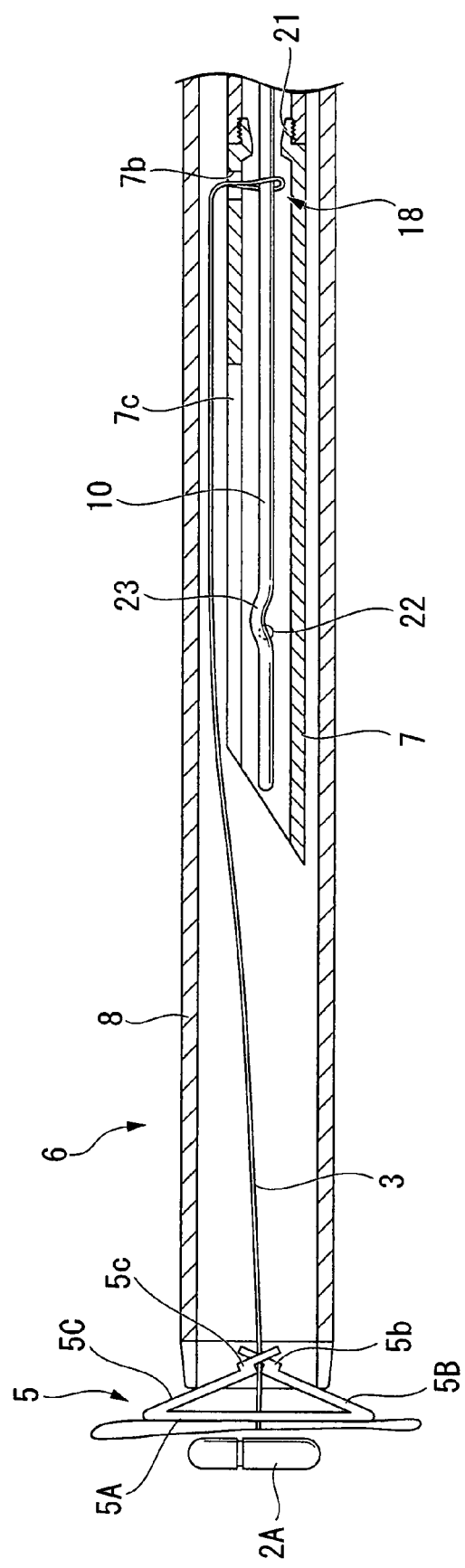
FIG. 38 is an explanatory diagram illustrating an operation of the suture instrument.

Next, as shown in FIG. 35, the needle slider 12 is allowed to retreat toward the proximal side relative to the operating section body 11. Accordingly, the puncture needle 7 is relatively drawn into the outer sheath 8 and the front end of the outer sheath 8 comes in contact with the stopper 5 of the suture tool 6, as shown in FIG. 36. As shown in FIG. 37, by moving the needle slider 12 to the proximal side, the distance between the stopper 5 and the anchors 2 is reduced. The reduction in distance between the anchors 2A and 2B allows the mucous membranes M5 and M6 hooked by the anchors 2A and 2B to be drawn to each other. Finally, as shown in FIG. 38, the stopper 5 comes in contact with the mucous membranes M5 and M6 and is fastened, thereby reducing the mucous-membrane lost portion M4.

Figure 39:
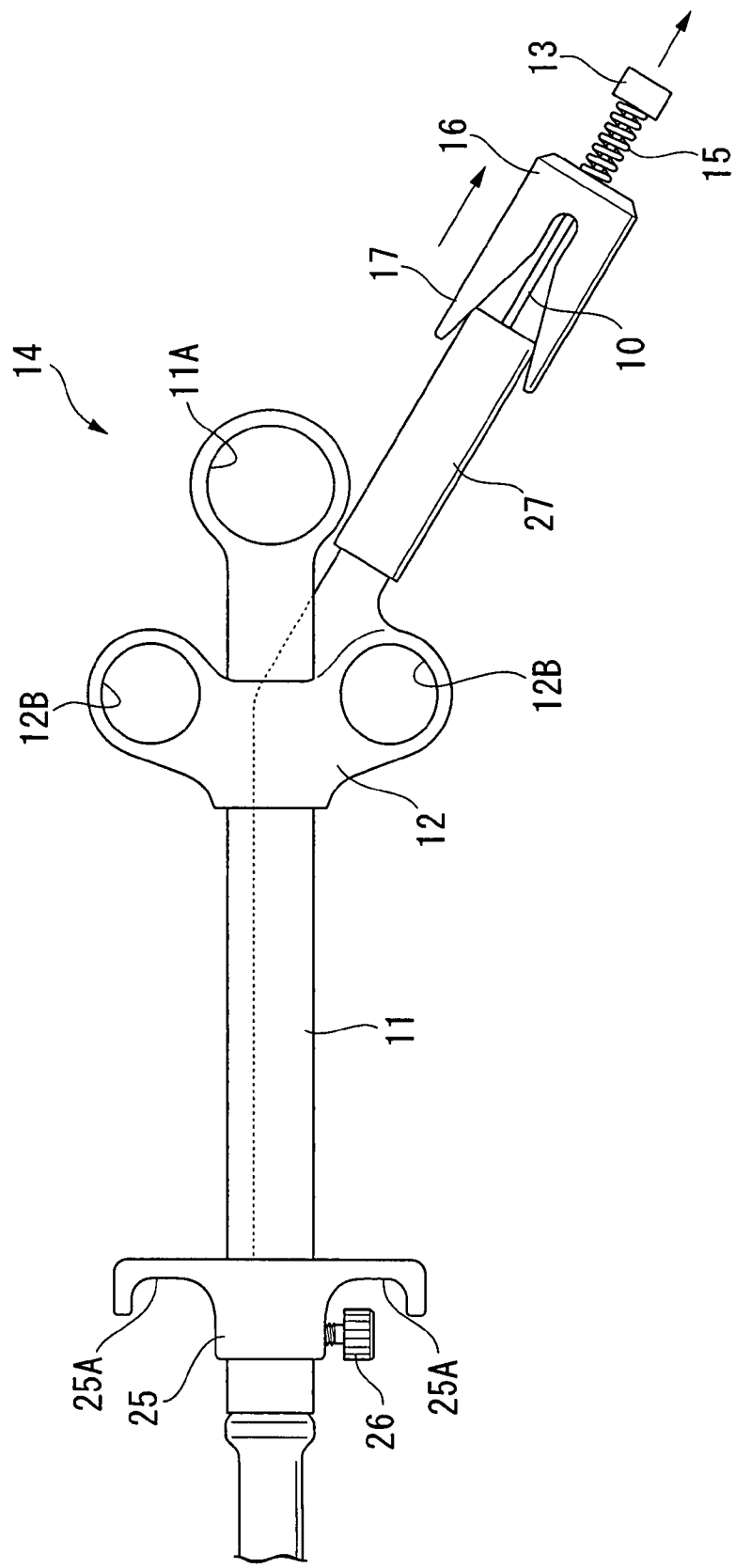
FIG. 39 is an explanatory diagram illustrating an operation of the suture instrument.
Figure 40:
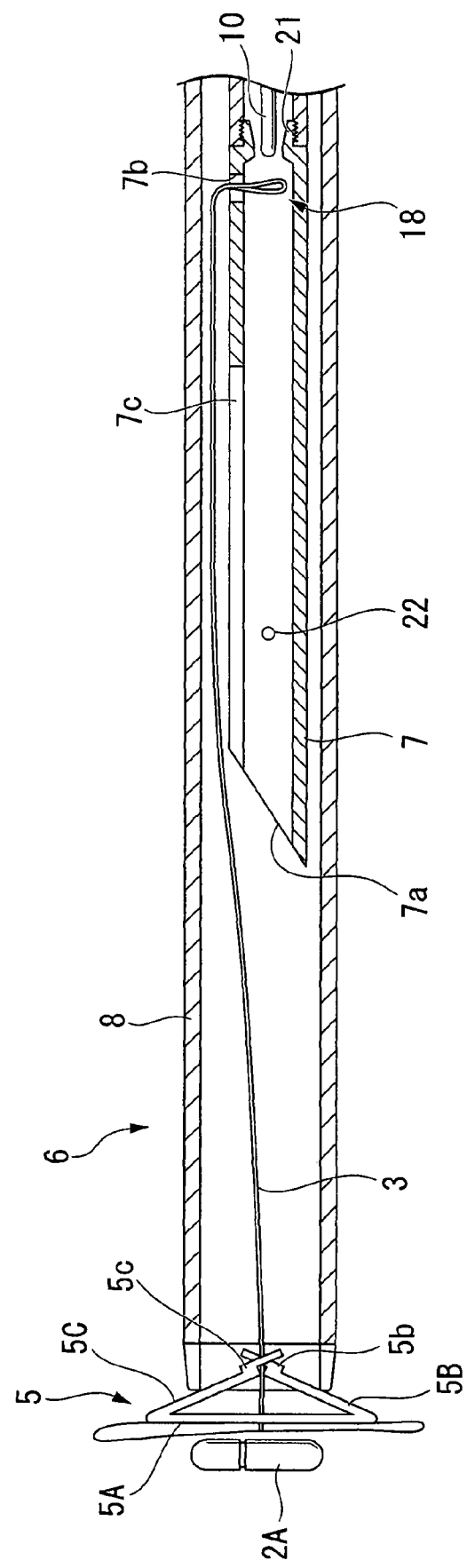
FIG. 40 is an explanatory diagram illustrating an operation of the suture instrument.
Figure 41:
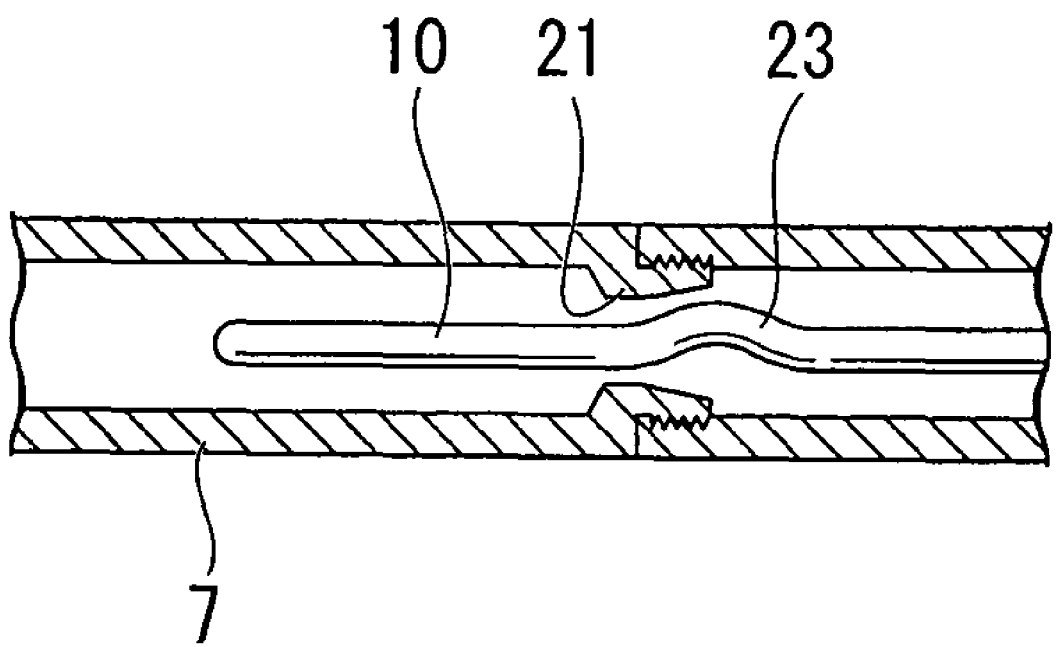
FIG. 41 is an explanatory diagram illustrating an operation of the suture instrument.
Figure 42:
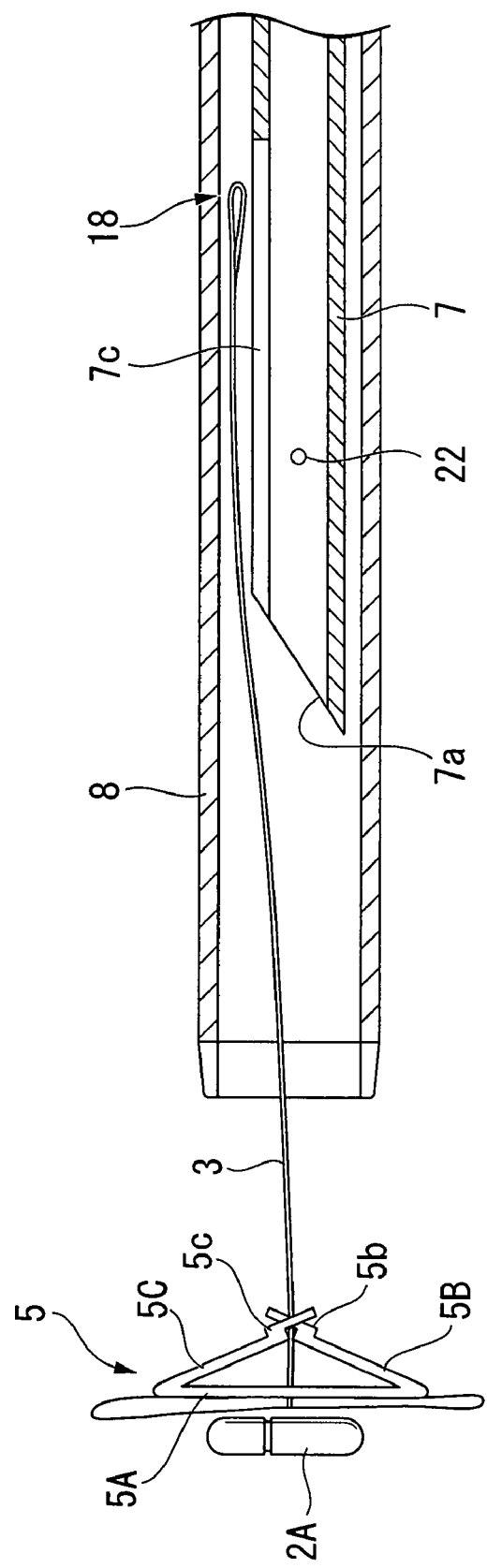
FIG. 42 is an explanatory diagram illustrating an operation of the suture instrument.
Figure 43:
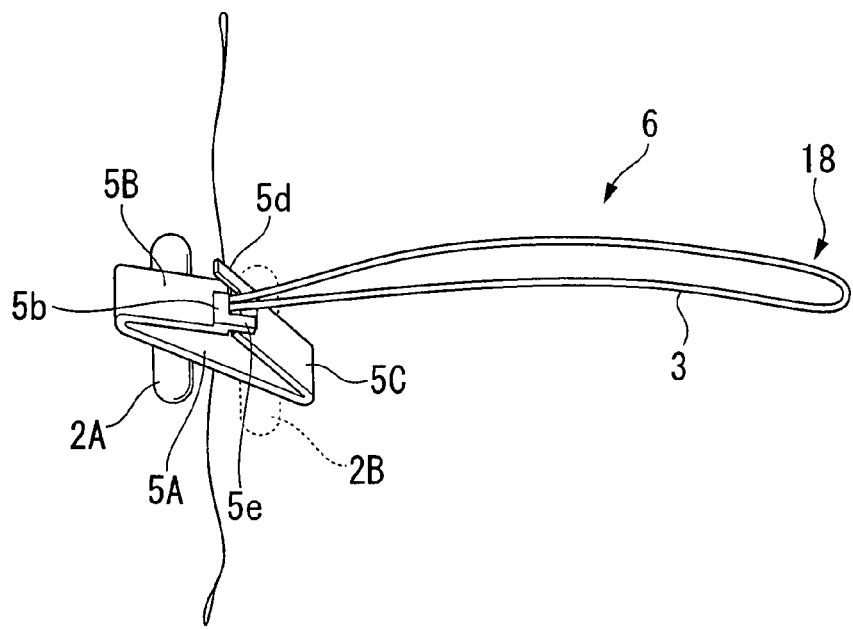
FIG. 43 is an explanatory diagram illustrating an operation of the suture instrument.
Figure 44:
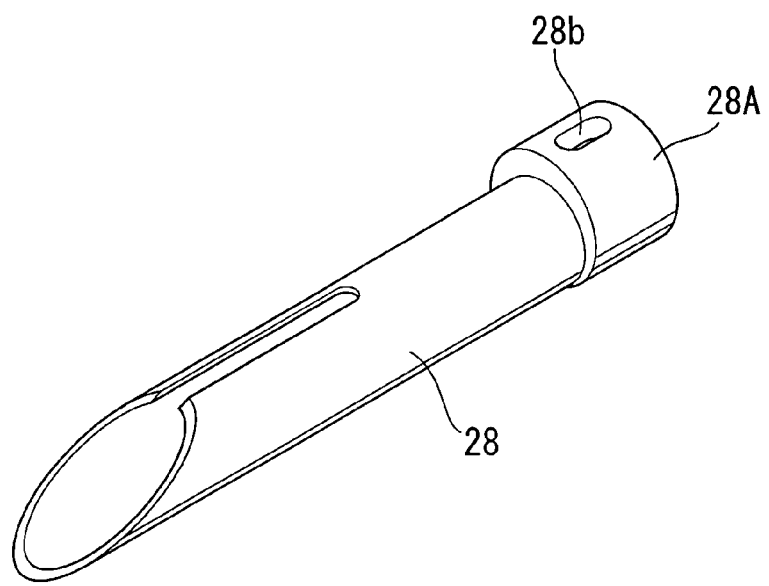
FIG. 44 is a perspective view illustrating a modified example of a suture needle of the suture instrument.
Figure 45:
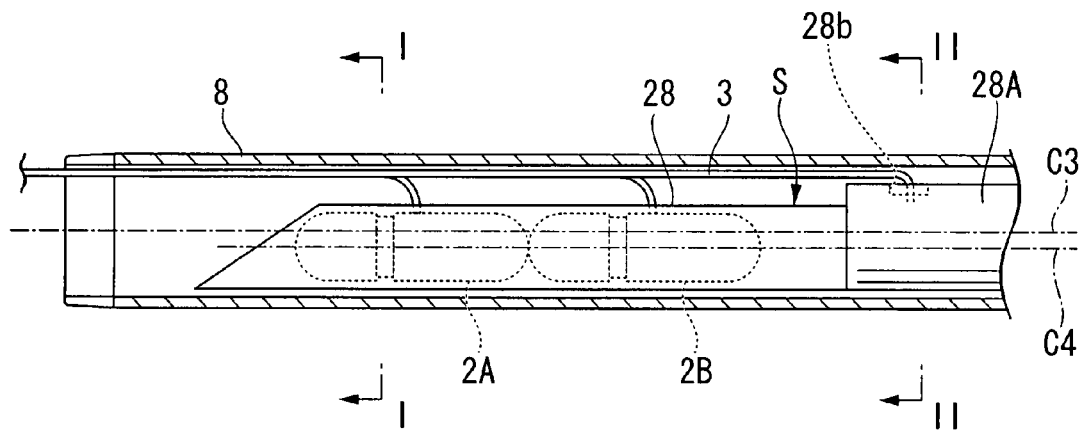
FIG. 45 is a perspective view illustrating a modified example of the suture needle of the suture instrument.
Figure 46:
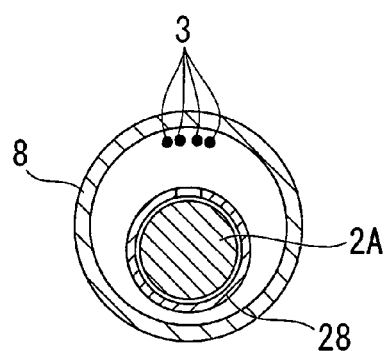
FIG. 46 is a cross-sectional view taken along line I-I of FIG. 45.
Figure 47:
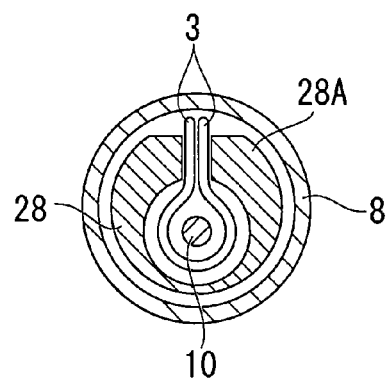
FIG. 47 is a cross-sectional view taken along line II-II of FIG. 45.

As shown in FIG. 39, the movable stopper 16 is allowed to retreat to the proximal side relative to the branch section 27. At this time, as shown in FIGS. 40 and 41, the loop 18 of the suture thread 3 is disengaged from the engaging portion 23 of the pusher 10 and the engaging portion 23 is resiliently deformed so as to pass over the restriction member 21, thereby moving the pusher 10 to the proximal side relative to the puncture needle 7. Here, when the suture instrument 1 or the endoscope insertion section EI is allowed to retreat apart from the mucous-membrane lost portion M4, the loop 18 is drawn from the introduction hole 7b of the puncture needle 7 to the outside of the puncture needle 7, as shown in FIG. 42. In this way, as shown in FIG. 43, the suture tool 6 is separated from the suture instrument 1 in the state where the suture thread 3 is maintained so as not to be loosened by the stopper 5, thereby detaining the suture tool 6.

According to the suture instrument 1, even when the sheath 9 is curved, it is possible to move the pusher operating section 13 relative to the operating section body 11 with the expansion and contraction of the sheath 9 by setting the movable stopper 16 to the movable state and setting the spring member 15 to the expansible state. By setting the movable stopper 16 to the fixed state by the use of the lock member 17 and setting the spring member 15 to the contractible state, it is possible to move the position of the front end 10a of the pusher 10 relative to the sheath 9 by a predetermined distance. Accordingly, regardless of the curvedness of the sheath 9, it is possible to allow the pusher 10 to precisely advance and retreat relative to the sheath 9 by a predetermined distance with a simple operation.

At this time, by grasping the lock member 17 to come in contact with the branch section 27, it is possible to allow the movable stopper 16 to be fixed to the operating section body 11. On the other hand, when the lock member 17 is not deformed, the movable stopper 16 can be set to the movable state relative to the branch section 27.

Since the movable stopper 16 and the branch section 27 are connected to each other with the spring member 15, the expanding and contracting amount of the spring member 15 can be easily controlled, thereby allowing the pusher 10 to advance and retreat with high precision.

The engaging portion 23 is disposed in the pusher 10. Accordingly, even after the puncture needle 7 punctures the biological tissue and the anchors 2 are detained by moving the pusher 10, the suture thread 3 can be held by the pusher 10. Therefore, by drawing the puncture needle 7 into the proximal side of the outer sheath 8 along with the pusher 10 in a state where the outer sheath 8 is in contact with the stopper 5 of the suture tool 6, it is possible to move the stopper 5 toward the anchors 2. Thereafter, by disengaging the suture thread 3 from the pusher 10, it is possible to detain the suture tool 6 in the biological tissue. Accordingly, it is possible to continuously perform the detention of the suture tool 6 and the suture, without replacing a plurality of treatment tools.

At this time, by introducing the loop 18 of the suture thread 3 into the puncture needle 7 through the introduction hole 7b of the puncture needle 7 and inserting the pusher 10 into the loop 18, it is possible to allow the loop 18 to easily engage with the engaging portion 23.

By allowing the needle slider 12 to advance and retreat relative to the operating section body 11, it is possible to allow the puncture needle 7 to protrude and retract relative to the outer sheath 8. By allowing the pusher operating section 13 to advance and retreat relative to the needle slider 12, it is possible to allow the pusher 10 to advance and retreat relative to the puncture needle 7. Here, since the branch section 27 is inclined about the operating section body 11, it is possible to continuously operate the needle slider 12 and the pusher operating section 13 without changing both portions at the time of operating both portions to advance and retreat.

The outer sheath 8 has a coil shape. As a result, even when the puncture needle 7 is allowed to retract into the outer sheath 8 with the suture thread 3 engaging with the engaging portion 23 and the stopper 5 of the suture thread 3 is pressed by the front end of the outer sheath 8, it can reliably endure the compressing force generated in the axis direction of the outer sheath 8.

The proximal side sheath 8B is covered with the resin tube 24. As a result, when the puncture needle 7 is extruded from the outer sheath 8, it can reliably endure the drawing force generated in the outer sheath 8.

As shown in FIG. 41, the restriction member 21 is disposed in the puncture needle 7. As a result, when the pusher 10 is inserted into the puncture needle 7 at the time of assembly, the pusher 10 can be inserted while coming in contact with the gentle slope portion on the proximal side of the restriction member 21, thereby easily performing the assembly work. On the other hand, when the pusher 10 is accidentally moved relatively toward the base end of the puncture needle 7 after the assembly, the engaging portion 23 comes in contact with the sharp slope portion of the restriction member 21, thereby restricting the further movement of the pusher 10.

According to the suture tool 6, when the suture thread 3 is sandwiched by the thick plate portions 5b and 5c of the front end of the pair of bent pieces 5B and 5C of the suture tool 6, the contact area between the pair of bent pieces 5B and 5C and the suture thread 3 can be increased more suitably, thereby reducing the stress generated in the pair of bent pieces 5B and 5C. Accordingly, the stopper 5 can maintain a stable fixing force to the biological tissue.

When the suture thread 3 is inserted through the stopper 5, the pair of bent pieces 5B and 5C are inclined about the base portion 5A. However, when the stopper 5 is moved relative to the suture thread 3 and is fixed to the biological tissue, the pair of bent pieces 5B and 5C and the base portion 5A become substantially parallel to each other similarly to the initial state. That is, since the pair of bent pieces 5B and 5C are returned to the initial state, the force for fixing the suture thread 3 is not reduced while moving the stopper 5. As a result, it is possible to satisfactorily suppress the movement of the bent pieces 5B and 5C relative to the suture thread 3 while the stopper 5 is detained.

Since the thick plate portions 5b and 5c and the engaging protrusions 5d and 5e engage with each other at the time of sandwiching the suture thread 3 by the use of the stopper 5, it is possible to satisfactorily prevent the mismatch between the bent pieces 5B and 5C due to the force having a direction intersecting the center axis C of the pair of bent pieces 5B and 5C.

As shown in FIGS. 44 to 47, the portion of a puncture needle 28 in which an introduction hole 28b is formed may be decentered to form a protruding portion 28A. This uses the space S formed between the puncture needle 28 and the outer sheath 8 because the center axis C3 of the outer sheath 8 and the center axis C4 of the puncture needle 28 are offset when the puncture needle 28 is disposed in the outer sheath 8.

Figure 48:
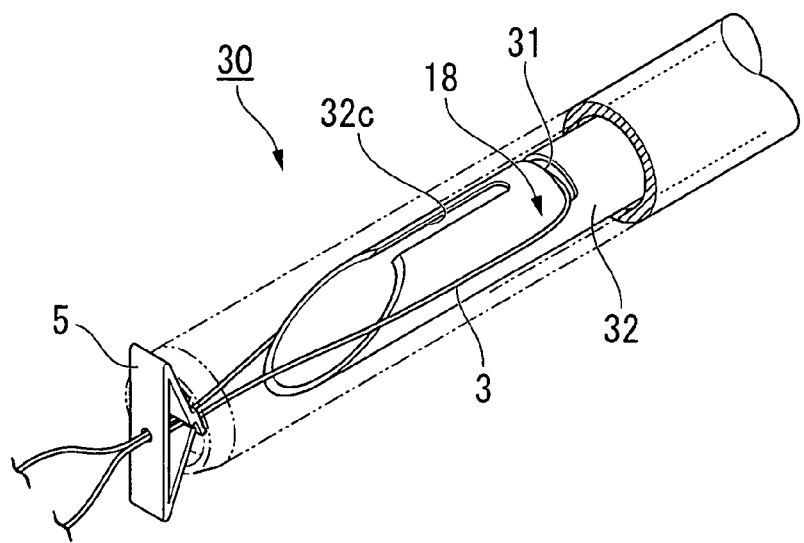
FIG. 48 is a partially enlarged perspective view illustrating a modified example of the suture instrument.

As shown in FIG. 48, an engaging portion 31 of a suture instrument 30 may be disposed in a slit shape in the side surface of a puncture needle 32.

In the suture instrument 30, the first anchor 2A and the second anchor 2B of the suture tool 6 are housed in series in the puncture needle 32, the suture thread 3 is allowed to protrude from a slit 32c, and the loop 18 is allowed to engage with the engaging portion 31, thereby maintaining the stopper 5 in a state where it is housed in the puncture needle 32.

Figure 49:
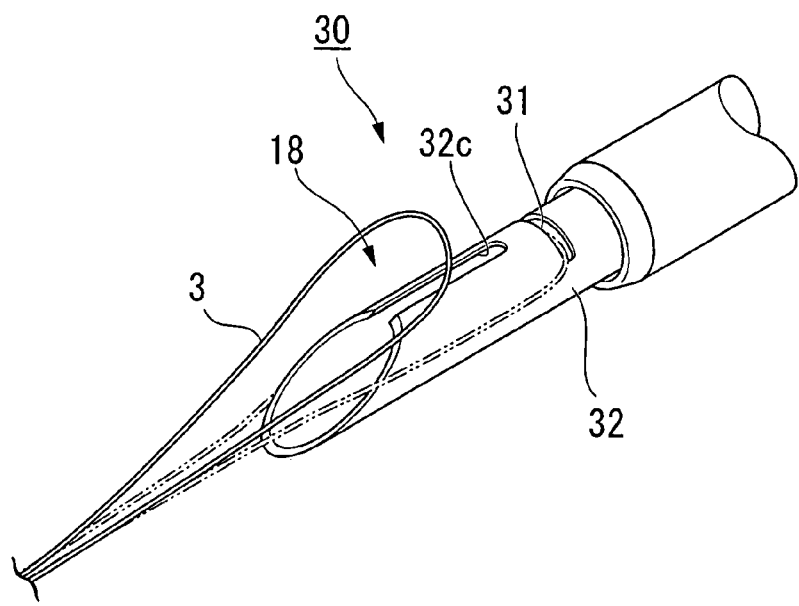
FIG. 49 is an explanatory diagram illustrating an operation of the suture instrument shown in FIG. 48.

By means of the same operation as the first embodiment, an anchor (not shown) of the suture tool 6 is detained. When the suture thread 3 is detached from the engaging portion 31, the puncture needle 32 is allowed to once protrude from the outer sheath 8 and the puncture needle 32 is shaken. At this time, the suture thread 3 is disengaged from the engaging portion 31, as shown in FIG. 49.

According to the suture instrument 30, since the engaging portion 31 has a slit shape, it is possible to allow the loop 18 to easily engage with the surface of the puncture needle 32 by hooking a part of the suture thread 3 thereto.

Figure 50:
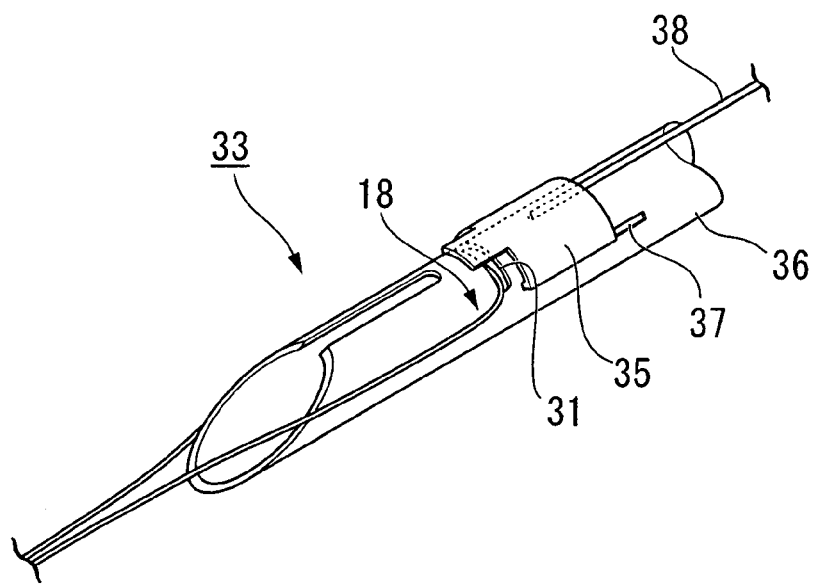
FIG. 50 is a partially enlarged perspective view illustrating a modified example of the suture instrument.

As shown in FIG. 50, a suture instrument 33 may include a lid 35 covering the engaging portion 31. The lid 35 engages with a guide groove 37 formed in the surface of a puncture needle 36 and is connected to a drawing member 38 so as to move along the guide groove 37.

According to the suture instrument 33, it is possible to satisfactorily prevent the suture thread 3 from erroneously departing from the engaging portion 31, by allowing the loop 18 to engage with the engaging portion 31 and then covering the engaging portion with the lid 35. By drawing the drawing member 38 to move the lid 35, it is possible to easily disengage the loop 18 from the engaging portion 31.

Figure 51:
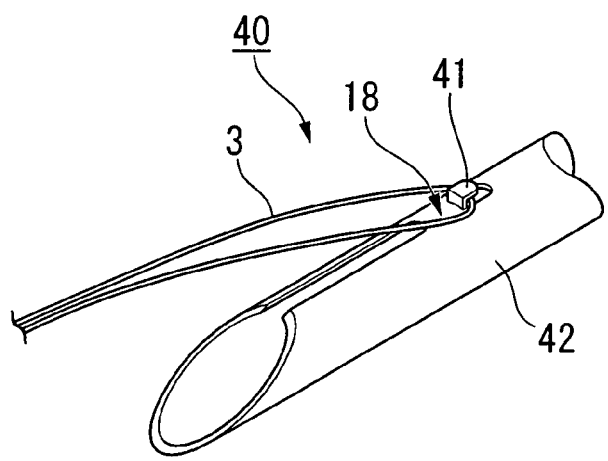
FIG. 51 is a partially enlarged perspective view illustrating a modified example of the suture instrument.

As shown in FIG. 51, an engaging portion 41 of a suture instrument 40 may be disposed to protrude from the side surface of a puncture needle 42.

The suture instrument 40 allows the loop 18 to engage with the engaging portion 41 and detains an anchor not shown. When the suture thread 3 is disengaged from the engaging portion 41, the suture thread 3 is disengaged from the engaging portion 41 by allowing the puncture needle 42 to once protrude from the outer sheath 8 and shaking the puncture needle 42.

According to the suture instrument 40, since the engaging portion 41 is disposed to protrude, it is possible to allow the loop 18 of the suture thread 3 to easily engage with the surface of the puncture needle 42.

Figure 52:
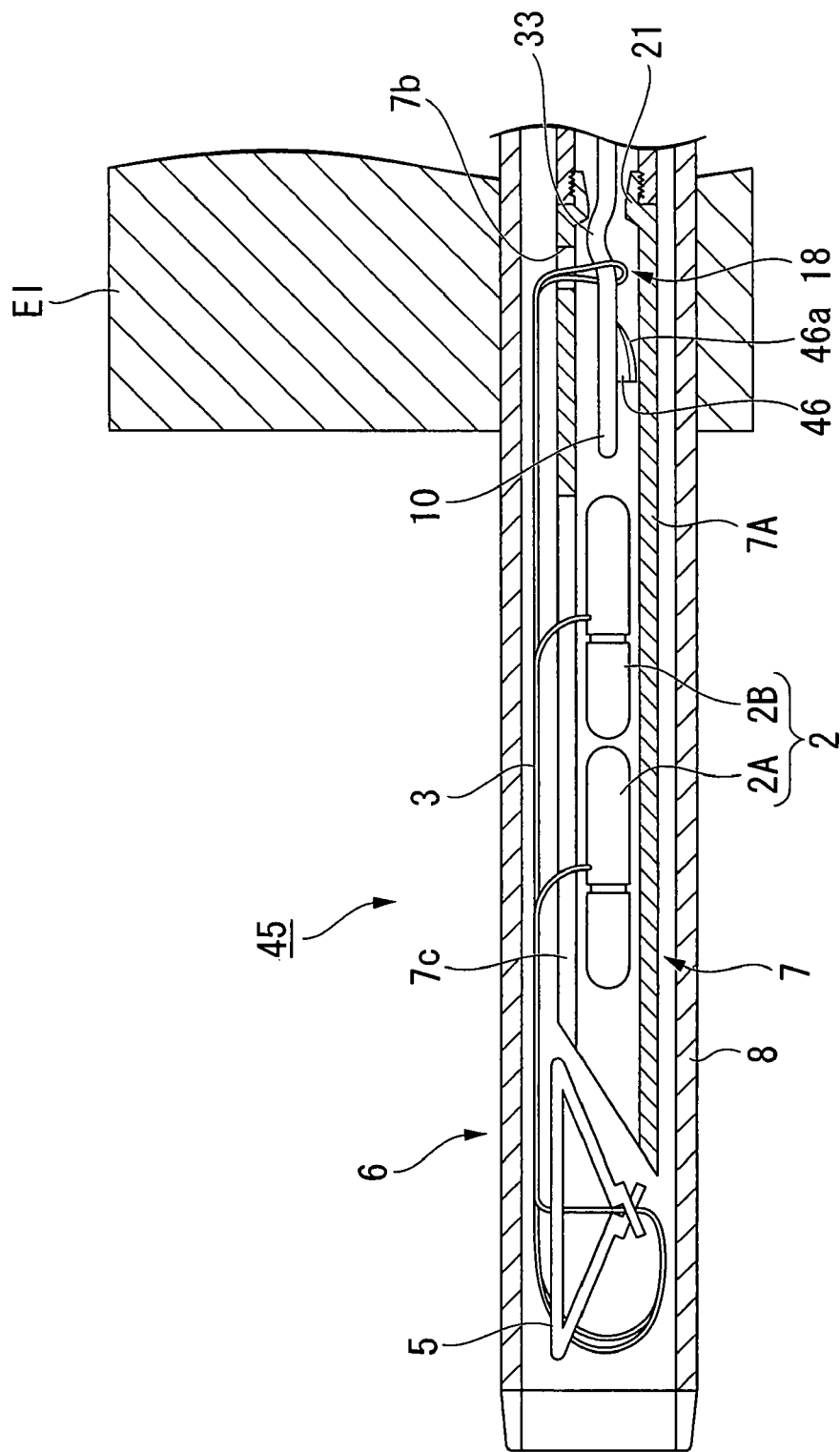
FIG. 52 is a partially enlarged perspective view illustrating a modified example of the suture instrument.

As shown in FIG. 52, the pusher 10 may be provided with a cutting edge 46 which can cut the suture thread 3 of a suture instrument 45.

Here, the cutting edge 46 is disposed closer to the front end of the pusher 10 than the engaging portion 23 by a shorter distance than the distance between the introduction hole 7b and the restriction member 21. A cutting edge face 46a is disposed toward only the proximal side.

In the suture instrument 45, by means of the same operation as the first embodiment, the first anchor 2A and the second anchor 2B of the suture tool 6 are housed in series in the puncture needle 7, the suture thread 3 is allowed to protrude from the slit 7c, and the loop 18 is introduced into the puncture needle 7 through the introduction hole 7b, and the front end of the pusher 10 is inserted into the loop 18, thereby allowing the loop 18 to engage with the engaging portion 23. Here, since the cutting edge face 46a is disposed to the proximal side, the loop 18 is not cut by the cutting edge 46 at the time of allowing the loop 18 to engage with the engaging portion 23.

When the suture thread 3 is disengaged from the engaging portion 23, the pusher 10 is drawn into the proximal side relative to the puncture needle 7. At this time, since the loop 18 comes in contact with the cutting edge face 46a, the loop 18 is cut and the suture thread 3 is disengaged from the engaging portion 23.

According to the suture instrument 45, by relatively moving the pusher 10 in a direction different from the direction in which the pusher 10 is inserted into the loop 18 of the suture thread 3, it is possible to easily cut the loop 18 with the cutting edge 46 and to disengage the loop 18 from the engaging portion 23.

Figure 53:
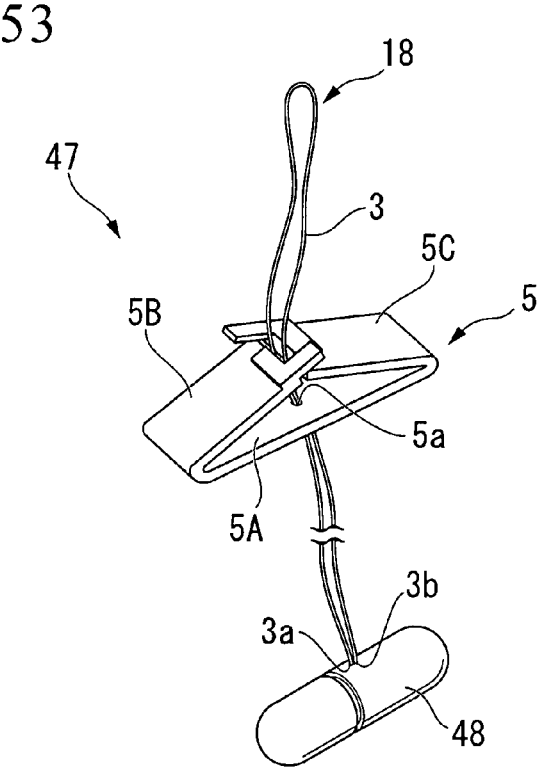
FIG. 53 is an entire perspective view illustrating a modified example of the suture instrument.

As shown in FIG. 53, when a suture tool 47 has only one anchor 48, the first end 3a and the second end 3b of the suture thread 3 may be connected to the same position of the anchor 48.

Figure 54:
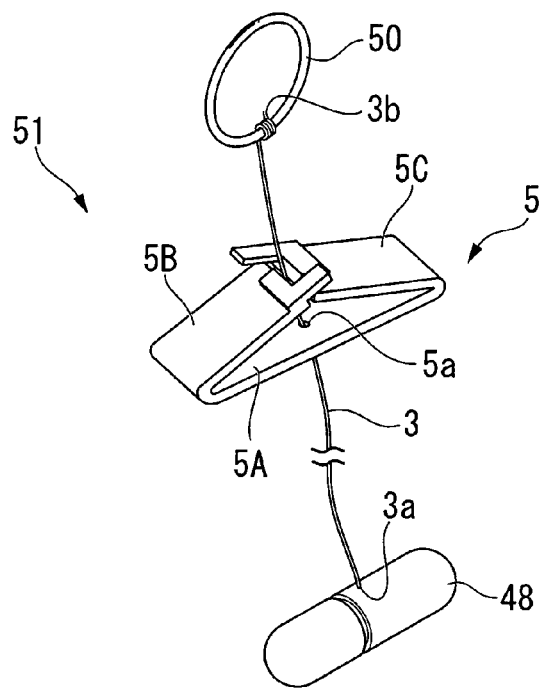
FIG. 54 is an entire perspective view illustrating a modified example of the suture instrument.

As shown in FIG. 54, a suture tool 51 in which the first end 3a of the suture thread 3 is connected to the anchor 48 and a ring 50 instead of the loop 18 is disposed at the second end 3b may be used.

Figure 55:
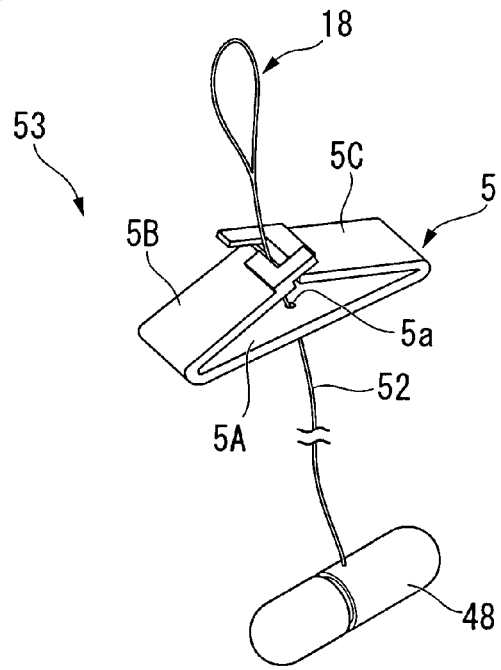
FIG. 55 is an entire perspective view illustrating a modified example of the suture instrument.
Figure 56:
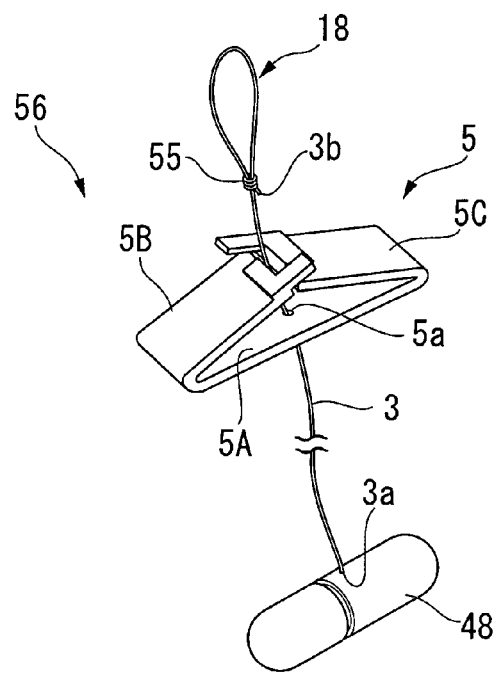
FIG. 56 is an entire perspective view illustrating a modified example of the suture instrument.
Figure 57:
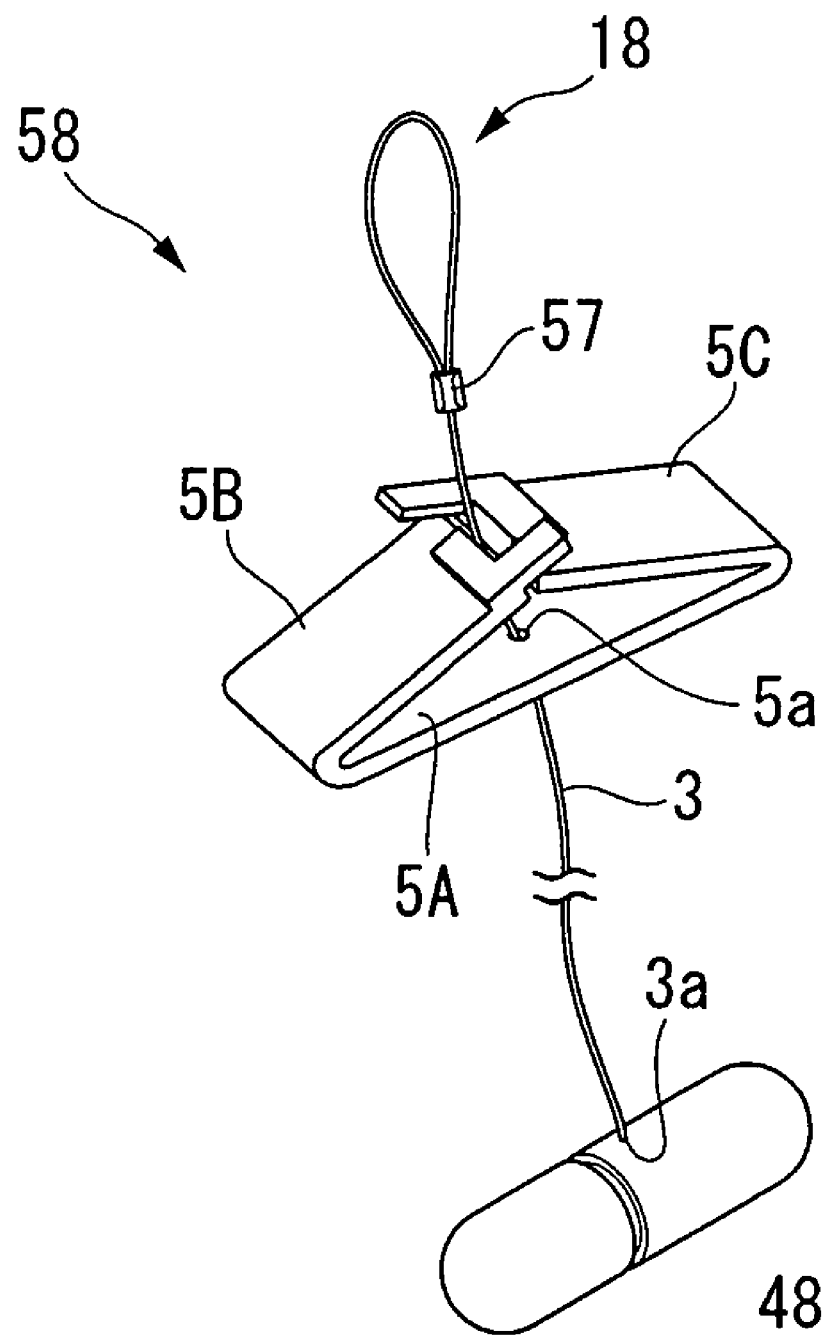
FIG. 57 is an entire perspective view illustrating a modified example of the suture instrument.

As shown in FIG. 55, a suture tool 53 in which a second end of a suture thread 52 is shaped in advance in a loop 18 may be used. As shown in FIG. 56, a suture tool 56 in which the loop 18 is formed by bending back the suture thread 3 and tying the second end 3b to an intermediate portion of the suture thread 3 to form a knot 55 may be used. Alternatively, as shown in FIG. 57, a suture tool 58 in which the loop 18 is formed by caulking the suture thread 3 with a caulking member 57 may be used.

Although exemplary embodiments of the invention have been described hitherto, the invention is not limited to the exemplary embodiments. The elements of the invention may be added, omitted, or replaced without departing from the gist of the invention. The invention is not restricted by the above description, but by only the scope of the appended claims.

What is claimed is:

1. A suture tool comprising an engaging member which is detained in a biological tissue, a suture thread which is drawn from the engaging member, and a fixing member which is penetrated by the suture thread and which restricts a looseness of the suture thread from the biological tissue anastomosed by the suture thread, wherein the fixing member includes:
    a base portion which has a thin and longitudinal plate shape and which has a through-hole through which the suture thread passes; and
    a pair of bent pieces of which ends are opposed to each other by bending both end portions of the base portion toward the center thereof, wherein each of the pair of bent pieces includes:
    a thin plate portion;
    a thick plate portion which is disposed at the end of the bent piece and which has a thickness thicker than the thin plate portion, the thick plate portion being provided on only a part of the bent piece in a width direction of the bent piece and disposed toward one lateral edge of the bent piece such that the thin plate portion is provided at the end of the bent piece between the thick plate portion and the other lateral edge of the bent piece, the one lateral edge and the other lateral edge being parallel to a longitudinal direction of the bent piece; and an engaging protrusion which protrudes from the thick plate portion along the longitudinal direction of the bent piece, and the engaging protrusion of one of the pair of bent pieces is fit into the thin plate portion of the other of the pair of bent pieces provided at the end between the thick plate portion and the other lateral edge.

2. The suture tool according to claim 1, wherein the pair of bent pieces are substantially parallel to the base portion.

3. The suture tool according to claim 1, wherein the thick plate portions integrally form a body along with the pair of bent pieces.

* * * * *